US007870005B2

(12) United States Patent
Arbogast et al.

(10) Patent No.: US 7,870,005 B2
(45) Date of Patent: Jan. 11, 2011

(54) SYSTEM, METHOD, AND COMPUTER PROGRAM PRODUCT FOR CONFIGURING AND PURCHASING A MEDICAL DEVICE

(75) Inventors: Robert E. Arbogast, Mount Sterling, OH (US); Michael Edward Hopkins, London, OH (US); James M. Colvin, Hilliard, OH (US); Mark William Ford, Jamestown, OH (US); Phillip Lee Harrison, Columbus, OH (US); Raymond Francis, Chesapeake, VA (US); Keith W. Justus, Columbus, OH (US); Rebecca L. Halley, Plain City, OH (US); Bradley A. Spitzer, Worthington, OH (US); Thomas D. Chamberlain, Columbus, OH (US); Eric L. Kershner, Grandview Heights, OH (US)

(73) Assignee: The Ohio Willow Wood Company, Mount Sterling, OH (US)

( * ) Notice: Subject to any disclaimer, the term of this patent is extended or adjusted under 35 U.S.C. 154(b) by 3404 days.

(21) Appl. No.: 09/893,535

(22) Filed: Jun. 29, 2001

(65) Prior Publication Data
US 2003/0009354 A1 Jan. 9, 2003

(51) Int. Cl.
*G06Q 10/00* (2006.01)
(52) U.S. Cl. .......................... 705/2; 700/163; 700/104; 700/214; 604/66; 705/1; 705/28; 705/29; 705/37; 717/120
(58) Field of Classification Search .................... 705/2, 705/29, 28, 12, 3, 37; 700/163, 104, 214; 717/120
See application file for complete search history.

(56) References Cited

U.S. PATENT DOCUMENTS

| | | | | |
|---|---|---|---|---|
| 4,491,725 A * | 1/1985 | Pritchard | ....................... | 705/2 |
| 5,301,105 A * | 4/1994 | Cummings, Jr. | ............... | 705/2 |
| 5,307,261 A * | 4/1994 | Maki et al. | .................... | 705/29 |
| 5,410,471 A | 4/1995 | Alyfuku et al. | | |
| 5,412,576 A * | 5/1995 | Hansen | ....................... | 700/104 |
| 5,432,703 A * | 7/1995 | Clynch et al. | ............... | 700/163 |
| 5,772,585 A | 6/1998 | Lavin et al. | | |
| 5,781,442 A * | 7/1998 | Engleson et al. | ............ | 700/214 |
| 5,999,908 A * | 12/1999 | Abelow | ......................... | 705/1 |
| 6,206,829 B1 | 3/2001 | Iliff | | |
| 6,325,756 B1 | 12/2001 | Webb et al. | | |
| 6,463,351 B1 * | 10/2002 | Clynch | ....................... | 700/163 |
| 6,581,204 B2 * | 6/2003 | DeBusk et al. | ............. | 717/120 |
| 2001/0051787 A1 * | 12/2001 | Haller et al. | .................. | 604/66 |
| 2002/0065758 A1 * | 5/2002 | Henley | ....................... | 705/37 |
| 2002/0099631 A1 * | 7/2002 | Vanker et al. | ................. | 705/28 |

* cited by examiner

*Primary Examiner*—Dilek B Cobanoglu
(74) *Attorney, Agent, or Firm*—Standley Law Group LLP

(57) ABSTRACT

A system, method, and computer program product for configuring a medical device. A personal data assistant is used by a practitioner to gather patient information. Patient information is transferred to a server, and three optional medical devices are configured as a "good," "better," and "best" alternative. One of the proposed options is selected customized by the practitioner prior to ordering. Order status may be obtained online, and historical patient and order information is maintained. A catalog of medical device components is also provided, the catalog items are either ordered "as is" or are customized through the customizer prior to ordering.

51 Claims, 19 Drawing Sheets

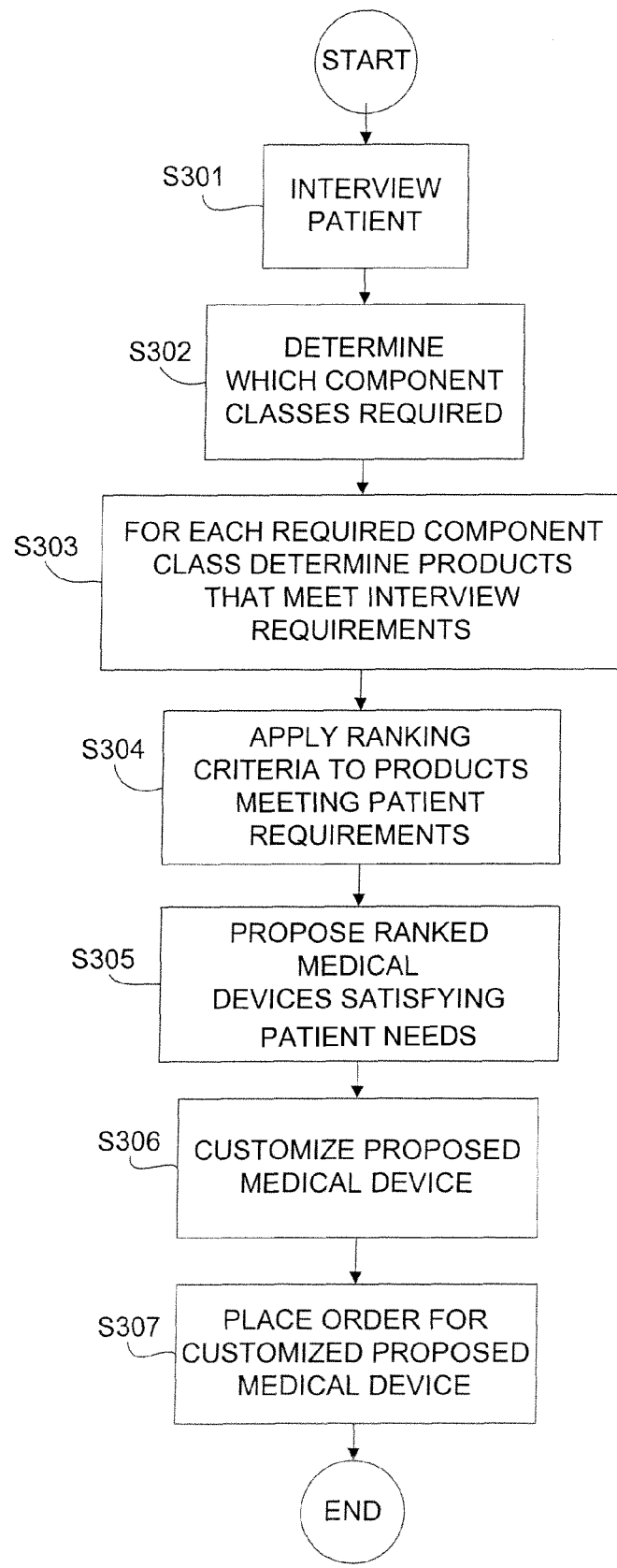

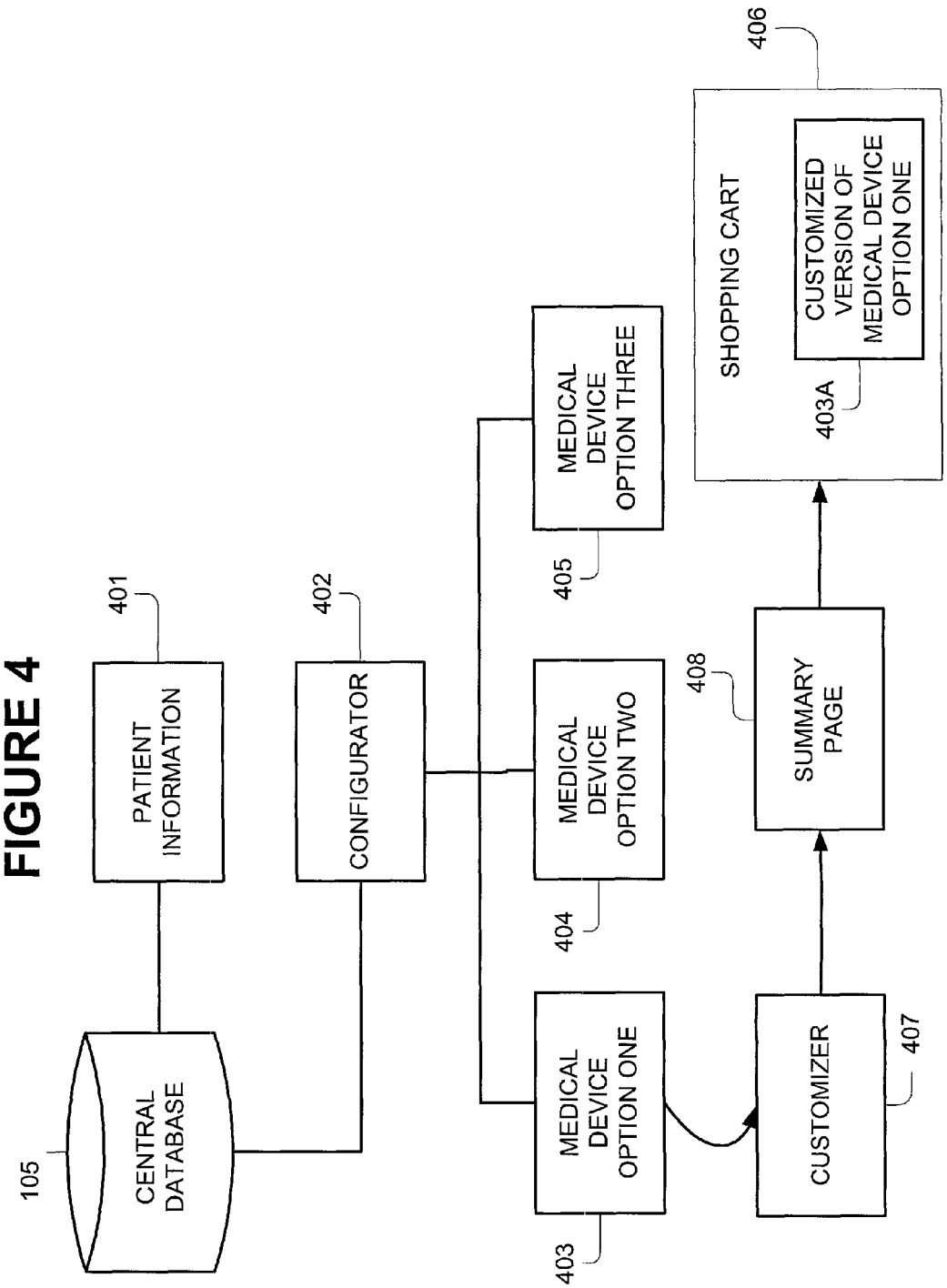

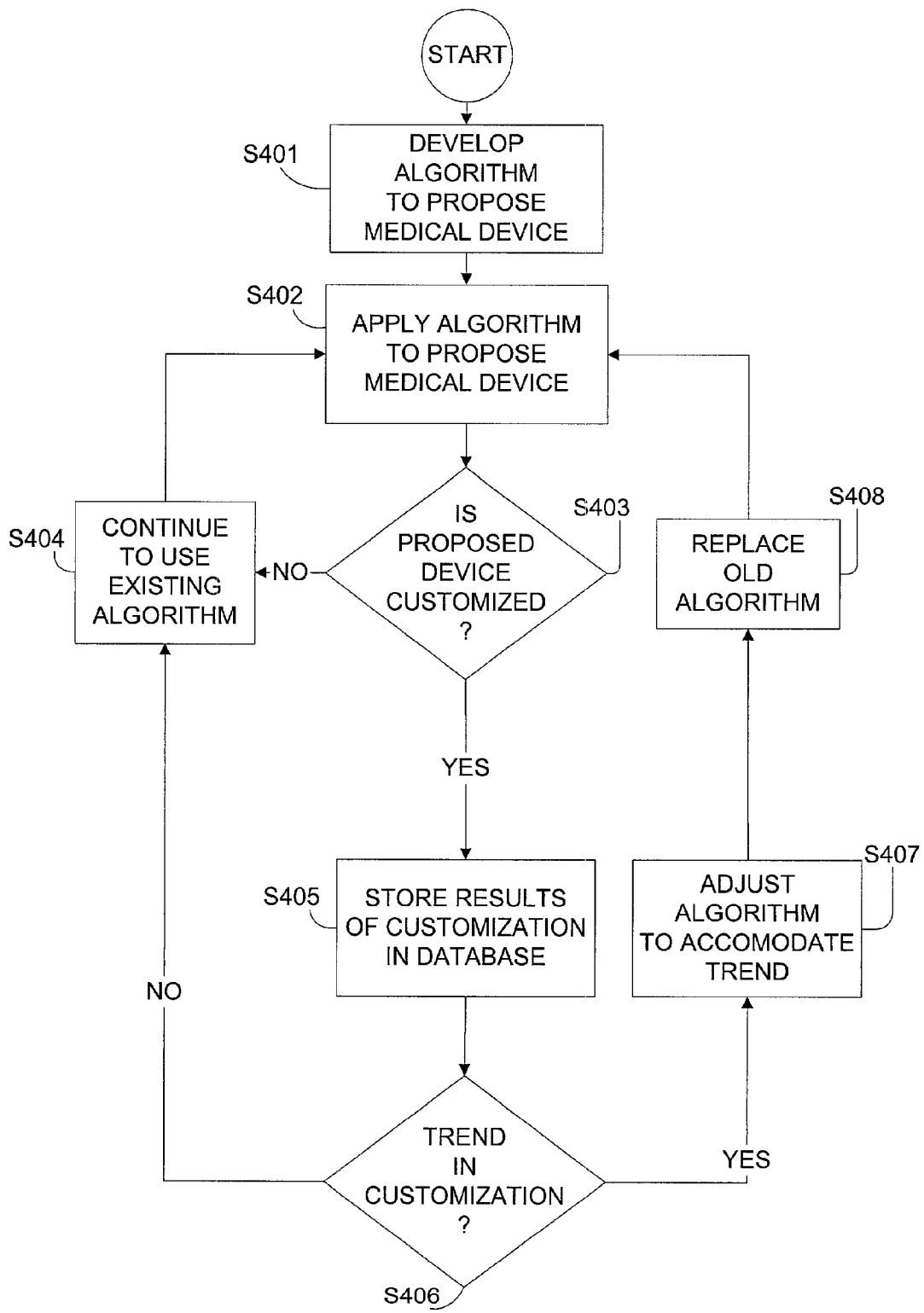

FIGURE 8

| | | | |
|---|---|---|---|
| FOOT A | UP TO 200 POUNDS | UP TO ACTIVITY LEVEL 3 | $100 | 1.1 |
| FOOT B | UP TO 175 POUNDS | UP TO ACTIVITY LEVEL 2 | $75 | 1.0 |
| FOOT C | UP TO 300 POUNDS | UP TO ACTIVITY LEVEL 4 | $300 | 1.7 |
| FOOT D | UP TO 200 POUNDS | UP TO ACTIVITY LEVEL 4 | $150 | 1.2 |
| FOOT E | UP TO 230 POUNDS | UP TO ACTIVITY LEVEL 2 | $100 | 1.5 |

SYSTEM, METHOD, AND COMPUTER PROGRAM PRODUCT FOR CONFIGURING AND PURCHASING A MEDICAL DEVICE

BACKGROUND OF THE INVENTION

1. Field of the Invention

The present invention relates to a system, method, and computer program product for configuring a medical device based on minimal input patient information.

2. Discussion of the Background

In order to configure a medical device (e.g., a prosthesis or an orthotic device) for a patient, a practitioner (e.g., a prosthetist or an orthotist) will meet with the patient and assess the patient's physical characteristics and needs. In the case of configuring a prosthesis, for example, a prosthetist will typically record information about the patient's physical characteristics on a paper form, including, for example, the patient's weight, height, size and shape of the residual limb, and the size and shape of the contralateral limb. The prosthetist will also gather information from the patient regarding their experience with other prostheses and their desires with respect to the new prosthesis. The prosthetist will also record any other pertinent information. In most cases, the physical measurements of the patient's residual limb are done manually, although some practitioners use digitizers (e.g., TracerCad running on a laptop computer) to gather the patient data electronically. Some prosthetists also take photographs or video clips of the patient's residual limb, the patient's current prosthesis and/or the patient's gait.

After evaluating the patient and gathering the information discussed above, the prosthetist begins the process of selecting components to be used in building a prosthesis for the patient. The components of a prosthesis may include, for example, a foot, an ankle, a shin, a knee, a socket interface, a suspension device, connectors, and a cosmetic covering. Each of these components of a prosthesis are available in numerous variations related to size, weight limit, stiffness, color, compatibility with other components, right side or left side, activity level of the patient, among others.

Conventionally, a practitioner uses ordering guidelines in printed catalogs to select the desired components of a medical device (e.g., a prosthesis or an orthotic device). Once a component is selected, the practitioner writes down the part number for that component on an order form, and then goes back to a different section of the catalog, or to a different catalog altogether, and uses another set of ordering guidelines to select the next component. The practitioner then writes down the part number for that component on the order form, or another order form, and continues this selection process until all of the components required for the prosthesis have been selected.

In order for the practitioner to determine the total price prior to placing the order, he or she needs to lookup the price for each component on one or more price lists, and then factor in any discounts that they may qualify for. Once a price has been determined for each of the components, and any applicable discounts have been applied, the prices of the individual components can be added up to determine the total price. Using this approach, the practitioner is typically unable to determine actual shipping costs, and therefore the price determination is at best an estimate. Furthermore, if the practitioner wants to determine the total weight of the components selected, he or she may or may not be able to get an approximate weight for an "average" component from the catalogs. If the practitioner is able to get estimates for each component, they will be able to determine an estimated total weight.

Because there are so many variations of each component of a medical device, and because these components are quite expensive, it is unlikely that a medical device facility will maintain an inventory of components that will be sufficient to fully configure any particular medical device. Therefore, in most cases, the practitioner orders the selected components from a manufacturer or distributor. Orders are normally placed by either phone or facsimile. To check on the status of an order, the practitioner is normally required to call the manufacturer or distributor, and sometimes, the practitioner is forced to contact the shipper so as to determine an exact status regarding their shipment.

As can be seen, the conventional procedure for selecting and ordering medical device components is a highly manual process that is inefficient and time consuming. Accordingly, under the conventional process, a practitioner is unable to maximize the amount of time he or she spends practicing their skill. These problems and inefficiencies are shared by other practitioners that configure medical devices as well, such as, for example, practitioners that configure orthotic devices.

Under the conventional approach, the various documents produced (e.g., evaluation forms, order forms, etc.) are maintained in a file for future reference. Accordingly, the conventional manual process does not produce products that are searchable for future use.

As technology advances, the number of new products and changes to existing products increases drastically. Accordingly, it is very difficult for a practitioner to stay current as to the state of the art of all components of medical devices. Therefore, when selecting components for a patient, the practitioner's options are limited to what he or she knows, and what is currently available in the most recent catalogs or product information that the practitioner has available. Based on this shortcoming of the conventional manual approach, it is quite possible that a patient's practitioner will be unaware of one or more components that may best meet that patient's needs.

Another disadvantage of the conventional manual process is that the practitioner must rely on their own experience to ensure that they have selected all of the components required to make up a complete medical device. Since each medical device is unique, it is quite possible that one or more components will be inadvertently left out of the practitioner's order, thereby requiring a second order that will delay the delivery of the medical device to the patient.

Yet another disadvantage of the conventional manual process is that when selecting and ordering the components, it is quite possible that errors will have been made either in recording the component number from the catalog, or in ordering the component over the telephone. Again, this problem will result in the necessity of a second order to correct the first order, and thereby delay the delivery of the medical device to the patient.

U.S. Pat. No. 5,972,035 to Blatchford describes a system and method for specifying an artificial limb. The system is limited to specifying prostheses, and requires that each component be individually selected, based on the ability of those components to interface with other previously selected components. By selecting compatible components, a complete prosthesis may be built. The system also requires that each component of a prosthetic device be specified, and that each of the components be compatible with the other components and connectors selected. Once the device has been fully specified, the complete prosthetic device, including connectors, may then be ordered. The Blatchford system is being developed as an Internet web site for configuring and ordering prostheses.

One of the disadvantages of a system requiring that an entire prosthetic device be specified is that it does not cater to the practitioner's need for options and flexibility. Many practitioners maintain inventory of certain components, and therefore oftentimes do not need to order each and every component of a medical device. Accordingly, it would be desirable to have the ability to pick and choose components of a medical device as well as to deselect components that the practitioner does not need to order.

Additionally, other systems have been developed for electronically ordering prosthetic devices or components, however, these systems do not include configuration or customization capabilities.

SUMMARY OF THE INVENTION

The inventors of the present invention have recognized that currently no methods, systems, or computer program products are available to provide practitioners with the desired flexibility in specifying and ordering medical devices that are tailored to each patient's needs. Accordingly, one object of the present invention is to provide a solution to this problem, as well as other problems and deficiencies associated with configuring and ordering medical devices in a way that is tailored to the patient's needs, as well as the practitioner's business.

The inventors of the present invention have recognized that each patient is unique, and therefore that the focus in configuring a medical device (e.g., a prosthesis or an orthotic device) should be on patient information, not technical component information as it is in conventional systems. Accordingly, a further object of the present invention is to provide a system, method, and computer program product through which medical devices may be configured based on patient information, as opposed to technical information relating to the components making up the medical device. The system of the present invention enables a practitioner to configure a solution for their patient based on the patient's answers to a series of screening questions and measurements taken of the patient.

The present inventors have further determined that it would be advantageous to have the ability to determine certain properties of the medical device as configured prior to placing an order. Accordingly, another object of the present invention is to provide summary information pertaining to a configured medical device, or portion thereof. The inventive system can provide an overall device weight, length, or other dimensions that are helpful to the practitioner in configuring a solution for a particular patient. Also, since patients have individualized cost constraints, cost information is available to the practitioner that alleviates the need for the practitioner to manually tally the individual component prices, to factor in any applicable discounts, and to determine a system price as configured.

The inventors of the present invention further recognized that there are many complexities and potential incompatibilities with adapters used in medical devices such as prostheses. Accordingly, a further object of the present invention is to provide a system, method, and computer program product in which the focus in configuring a medical is placed on the system components, rather than the adapters and compatibility issues between components. The inventors of the present invention have recognized that practitioners understand these complexities, and therefore, should not be limited when specifying a solution for a patient. Accordingly, the present invention allows practitioners to flexibly configure a solution for their patients, by either changing or omitting connectors and adapters, as they desire. This approach allows practitioners, who often have their own ways of connecting components and who often have supplies of their preferred connectors readily available on hand, to order the major components of a medical device without being required to order connectors and adapters that they do not need. Furthermore, the present invention does not limit a practitioner as to the options available when configuring a medical device. For example, using the system of the present invention, the practitioner will be presented with three alternative configurations that meet the needs of the patient based on a minimal amount of input patient information. The practitioner may then further customize one of those options to meet the particular needs of the patient. In doing so, the practitioner may rely on their expertise in selecting additional components, swapping components, or deselecting components from the selected system to arrive at the best solution for their patient.

The inventors of the present invention further recognized the value of providing flexibility regarding the input device that may be used by a practitioner depending on their personal preferences. The present inventors recognized that the system should provide not only a traditional keyboard and mouse entry through a personal computer graphical user interface, but also a personal data assistant-based (PDA) interface that is convenient for use during a patient interview to reduce errors and to eliminate redundant data entry. Accordingly, another object of the present invention is to provide an interface that may be hosted on a personal computer or a PDA for use by a practitioner during a patient interview. The PDA can then download the patient information for use in configuring a solution for that patient.

The inventors of the present invention further recognized the value of providing interfaces to other equipment for use during a patient evaluation. By having the ability to accept input from a variety of input devices, the system can support new techniques used by practitioners in fitting and configuring devices for their patients. Accordingly, yet another object of the present invention is to provide an interface capability for inputting patient information from, for example, a digitizer, a digital camera, or a digital video camera.

The inventors of the present invention further recognized that recent advances in health care business systems make it desirable to allow for the integration of a medical device configuration tool with a variety of other applications related to the practitioner's business. Accordingly, another object of the present invention is to provide a medical device configuration system that may be integrated with a variety of patient management and office management systems. For example, the system of the present invention includes, for example, patient identification information, reimbursement code information, and patient historical information that allows the system to interface with, for example, commercially available patient management systems and billing systems, thereby reducing the need for redundant data entry to the various systems used in running a practitioner's practice. This information is also used by the system of the present invention to populate template letters of necessity that are used to obtain approval for funding from the patient's payment source.

The above described and other objects are addressed by the present invention, which includes a novel computer-based system, method, and computer program product through which a practitioner may enter patient-specific information through, for example, a personal data assistant (PDA). The information is processed to arrive at three potential medical device systems having the major components that satisfy the patient-specific needs. The three potential solutions are ranked according to some criteria (e.g., cost, weight, functionality, inventory, etc.). The practitioner may then select one of the potential solutions and provide further refinements to it prior to placing an order. These refinements may include, for example, changing out proposed components or deselecting those portions of the suggested system that the practitioner does not wish to order. Since the system provides complete solutions including all of the major components for a device based on patient-specific information, the practitioner is not required to work through the many complexities in arriving at the suggested systems. Accordingly, practitioners using the system of the present invention can focus more of their time on the patient-oriented aspects of their business, and less time dealing with the complexities of configuring medical devices for their patients.

In one embodiment, the present invention is implemented as a system for configuring a medical device based on minimal input information, the required input information being patient-related data rather than device component information. The system includes a PDA through which a practitioner enters patient-related information. The information is processed to arrive at three suggested medical device systems based on the input patient information that are ranked according to some criteria. The practitioner may then select one of the complete systems and customize it to further meet the needs of a particular patient. The system of the present invention includes the ability to order either a complete system, or a subset of a system, based on the practitioner's particular needs. Practitioner-specific information is maintained in a "My Space" portion of a Internet web site. Practitioners may check on past and current orders placed through the system, or save patient or order-specific data for later reference. Patient information is maintained such that the system of the present invention may interface with, for example, patient management systems, reimbursement systems, and billing systems alleviating the need for redundant data entry.

In other embodiments of the present invention, patient-related information may be input into the system from a variety of devices through interfaces to the PDA or computer, for example, a digitizer for providing a digitized image of a stump, a digital camera, or a digital video device.

Consistent with the title of this section, the above summary is not intended to be an exhaustive discussion of all the features or embodiments of the present invention. A more complete, although not necessarily exhaustive, description of the features and embodiments of the invention is found in the section entitled "DESCRIPTION OF THE PREFERRED EMBODIMENTS."

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein:

FIG. 3 is a flow diagram illustrating a process through which a medical device satisfying a particular patient's needs is configured and ordered according to one embodiment of the present invention;

FIG. 4 is a block diagram showing the presentment of the three options based on input patient information, the customization of one of those options, and the selection and ordering of a customized version of one of those options according to one embodiment of the present invention;

FIG. 4A is a flow diagram illustrating a process through which an algorithm of the configurator is adjusted based on trends in customization according to one embodiment of the present invention;

FIG. 8 illustrates exemplary data structures containing descriptive information for medical device component options according to one embodiment of the present invention;

FIGS. 10A-10H illustrate exemplary screens of a practitioner's user interface according to one embodiment of the present invention.

DESCRIPTION OF THE PREFERRED EMBODIMENTS

Figure 1:
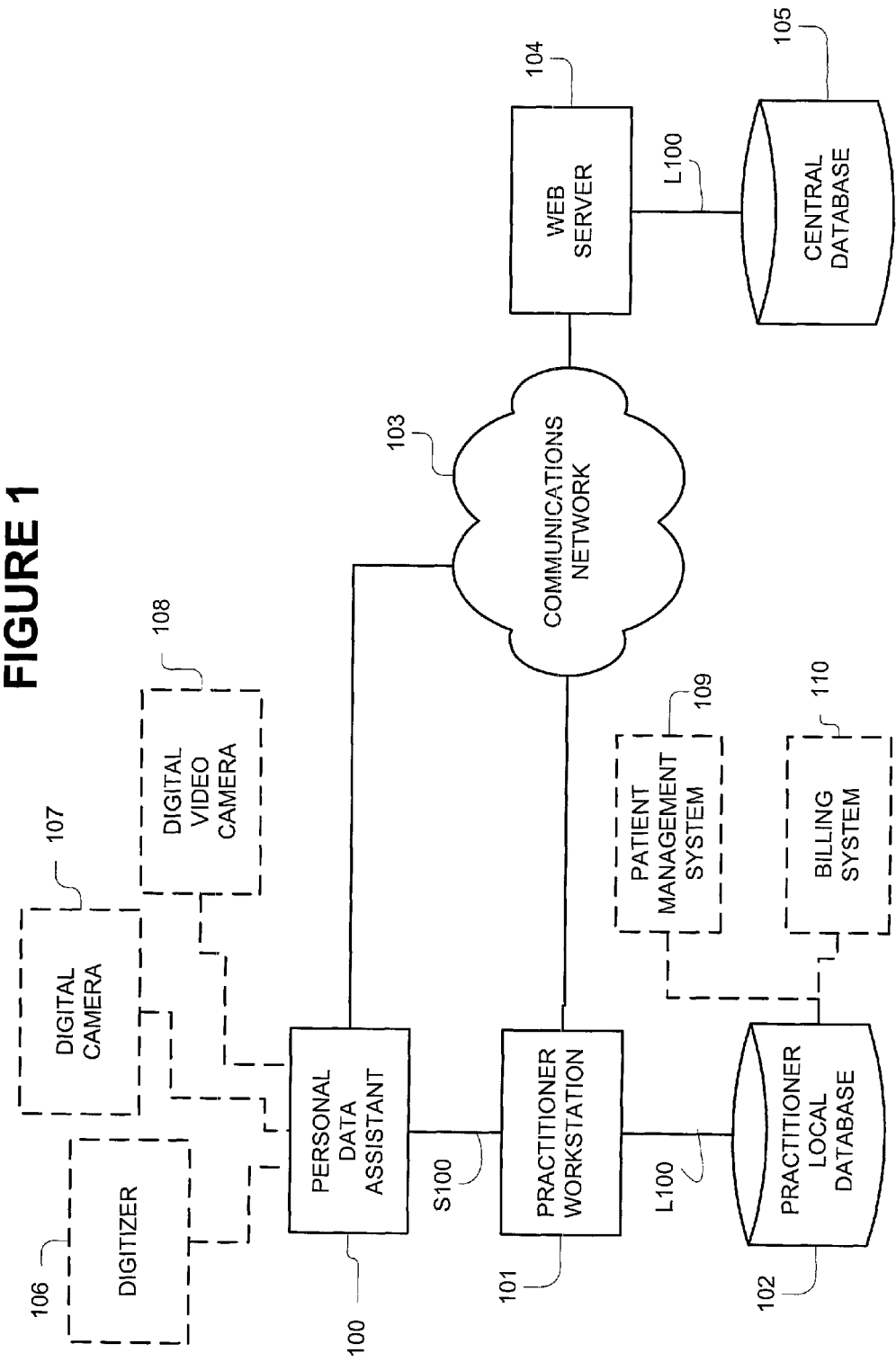
FIG. 1 is a block diagram of a typical system configuration of a system for configuring and ordering a medical device according to one embodiment of the present invention.

Referring now to the drawings, wherein like reference numerals designate identical or corresponding parts throughout the several views, and more particularly to FIG. 1 thereof, which is a block diagram of a system for configuring and ordering a medical device. As shown in FIG. 1, the system includes a personal data assistant (PDA) 100, a practitioner workstation 101, a practitioner local database 102, a communications network 103, a web server 104, and a central database 105. In some embodiments of the present invention, the system includes a digitizer 106, a digital camera 107, and/or a digital video camera 108.

The PDA 100 is used by the practitioner for gathering and recording patient information. In one embodiment of the present invention, the practitioner enters the patient information directly at the practitioner workstation 101. The practitioner workstation 101 maintains patient information in the practitioner local database 102. The practitioner workstation 101 is implemented using the computer system 1101 of FIG. 11, for example, but also may be any other suitable personal computer (PC), workstation, server, or device for synchronizing with the personal data assistant 100, maintaining information in the practitioner local database 102, and communicating with the web server 104 via the communications network 103.

The practitioner local database 102 is a digital repository that may be implemented, for example, through a commercially available relational database management system (RDBMS) based on the structured query language (SQL) such as, for example, ORACLE, SYBASE, INFORMIX, DB/2, or MICROSOFT SQL SERVER, through an object-oriented database management system (ODBMS), or through custom database management software. In one embodiment, the practitioner local database 102 contains information pertaining to all of the practitioner's patients. The practitioner local database 102 may reside on a storage device of the practitioner workstation 101, or reside on another device connected to the practitioner workstation 101, for example, by way of a local area network L100 or other communications link such as a virtual private network, wireless link, or Internet-enabled link.

In one embodiment of the present invention, the practitioner local database shares information with external applications, including, but not limited to, a patient management system 109 and a billing system 110. Accordingly, the practitioner local database includes not only information regarding the medical devices, but also patient identification information, insurance reimbursement information (e.g., L code information or other information for populating template letters of necessity), and other information that allows the system of the present invention to integrate with the other patient and business applications used by practitioners in running their practice.

As discussed above, a practitioner may enter patient information through either the PDA 100, or the practitioner workstation 101. In one embodiment of the present invention, the information input to the PDA 100 is synchronized with the practitioner workstation 101 through a connection S100 to a serial port of the practitioner workstation 101, or other communications link such as a wireless link or infrared link.

In other embodiments of the present invention, external devices may be used to gather patient information. For example, a digitizer 106, a digital camera 107, and/or a digital video camera 108 may be used to further gather patient information. The information input to the digitizer 106, digital camera 107, or digital video camera 108 may be transferred to the practitioner local database 102 via a connection to the PDA 100, or via a connection to the practitioner workstation 101 (not shown). Information may be transferred between the digitizer 106, digital camera 107, and digital video camera 108, for example, through a wired connection, or other communications link such as a wireless link or an infrared link.

Once the patient information has been gathered, the patient information is sent to the web server 104 via a communications network 103. In one embodiment of the present invention, the communications network 103 is the Internet.

Figure 11:
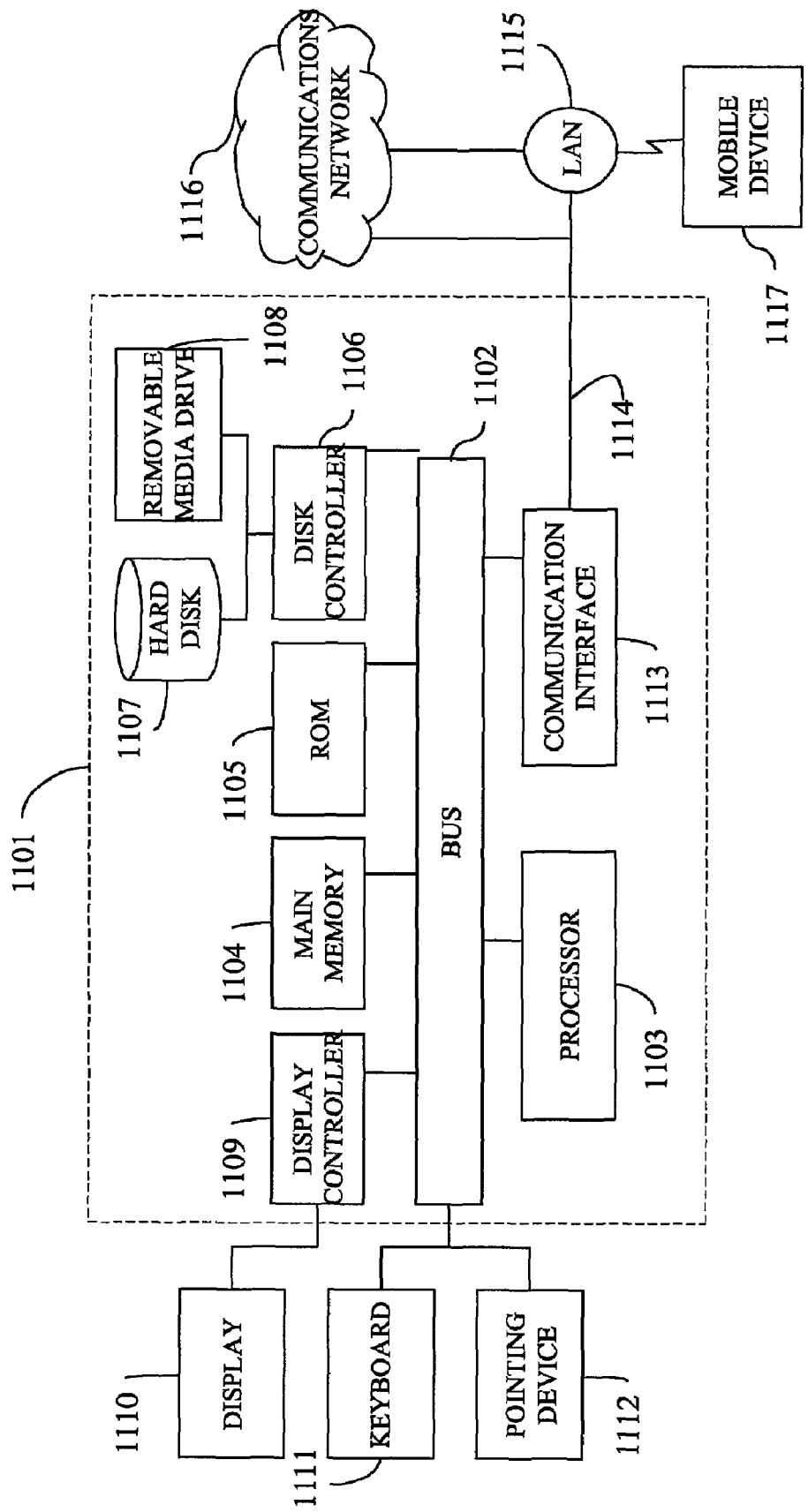
FIG. 11 is an exemplary computer system programmed to perform one or more of the special purpose functions of the present invention.

The web server 104 may be implemented using the computer system 1101 of FIG. 11, for example, or any other suitable PC, workstation, server, or other device for hosting an interface through which practitioners may interact with information maintained in the central database 105. In one embodiment of the present invention, the user interface provided by the web server 104 is a world wide web interface accessible through the communications network 103 (e.g., the Internet) via commercially available web browser tools including, but not limited to, INTERNET EXPLORER, available from Microsoft Corporation and NETSCAPE NAVIGATOR, available from Netscape Communications Corporation. The commercially available web browser tool running on the practitioner workstation 101 or the PDA 100 provides accessibility to applications running on the web server 104 providing access to information in the central database 105.

The central database 105 is a digital repository that may be implemented, for example, through a commercially available RDBMS based on SQL, such as ORACLE, SYBASE, INFORMIX, DB/2, or MICROSOFT SQL SERVER, through an ODBMS, or through custom database management software. In one embodiment of the present invention, the central database 105 includes information related to medical device (e.g., prostheses or orthotic devices) components and configurations, as well as patient information provided via the web server 104 from various practitioners interacting with the system.

The web server 104 hosts applications for receiving patient information from a practitioner workstation 101, or from a practitioner's PDA 100 via the communications network 103. Furthermore, the web server 104 hosts applications for storing patient-specific information in the central database 105, and processing patient information so as to determine optional configurations of medical devices made up of medical device components that best meet a particular patient's needs. The optional medical device configurations are tailored to an individual patient's needs and made up of components, the descriptions of which are stored in the central database 105. The web server 104 also supports applications for managing the central database 105. For example, the web server 104 hosts applications for maintaining practitioner-specific information, such as, for example, historical information on a practitioner's prior patients. Furthermore, the web server 104 hosts applications for maintaining the "catalog" of medical device components within the central database 105.

The inventors of the present invention have recognized that maintaining a medical device fabrication shop is an inefficient and expensive component of a practitioner's business. As an example of how information provided from external devices may be used, in one embodiment of the present invention, the system allows a practitioner to completely outsource the fabrication of the medical device, thereby saving the practitioner the cost of maintaining their own fabrication shop. In this example, the practitioner interviews the patient providing the patient-specific information via the PDA 100 or practitioner workstation 101 interface. If required for assuring a proper fit, the practitioner then digitizes the patient's stump or limb using an external digitizer 106 connected via a link to either the PDA 100 or the practitioner workstation 101. The digitized image of the stump or limb, along with the patient interview information, is sent to the web server 104 via the communications network 103. The patient interview information along with the digitized image of the stump or limb provides sufficient information for the medical device vendor to not only provide the components, but also to completely fabricate the system to fit the patient based on the digitized image of the patient's stump or limb. By outsourcing the fabrication of the medical devices, practitioners are able to increase their efficiency, eliminate the overhead associated with maintaining a fabrication shop, and to concentrate a larger portion of their time on the more enjoyable and more profitable patient care aspect of their practice.

Extending this example further, with the system of the present invention, a practitioner can practice without an office. A practitioner equipped with the PDA 100 and a digitizer 106 according to the present invention could practice out of a virtual office, calling on patients in person, recording information via the PDA 100 and obtaining digitized images with the digitizer 106. Information gathered from patient visits will be maintained in a practitioner local database 102 and sufficient information, including, for example, patient interview information and digitized images, will be transferred to the central database 105 from which the vendor will fabricate the desired devices and ship them to the practitioner to deliver to the patient.

Figure 2:
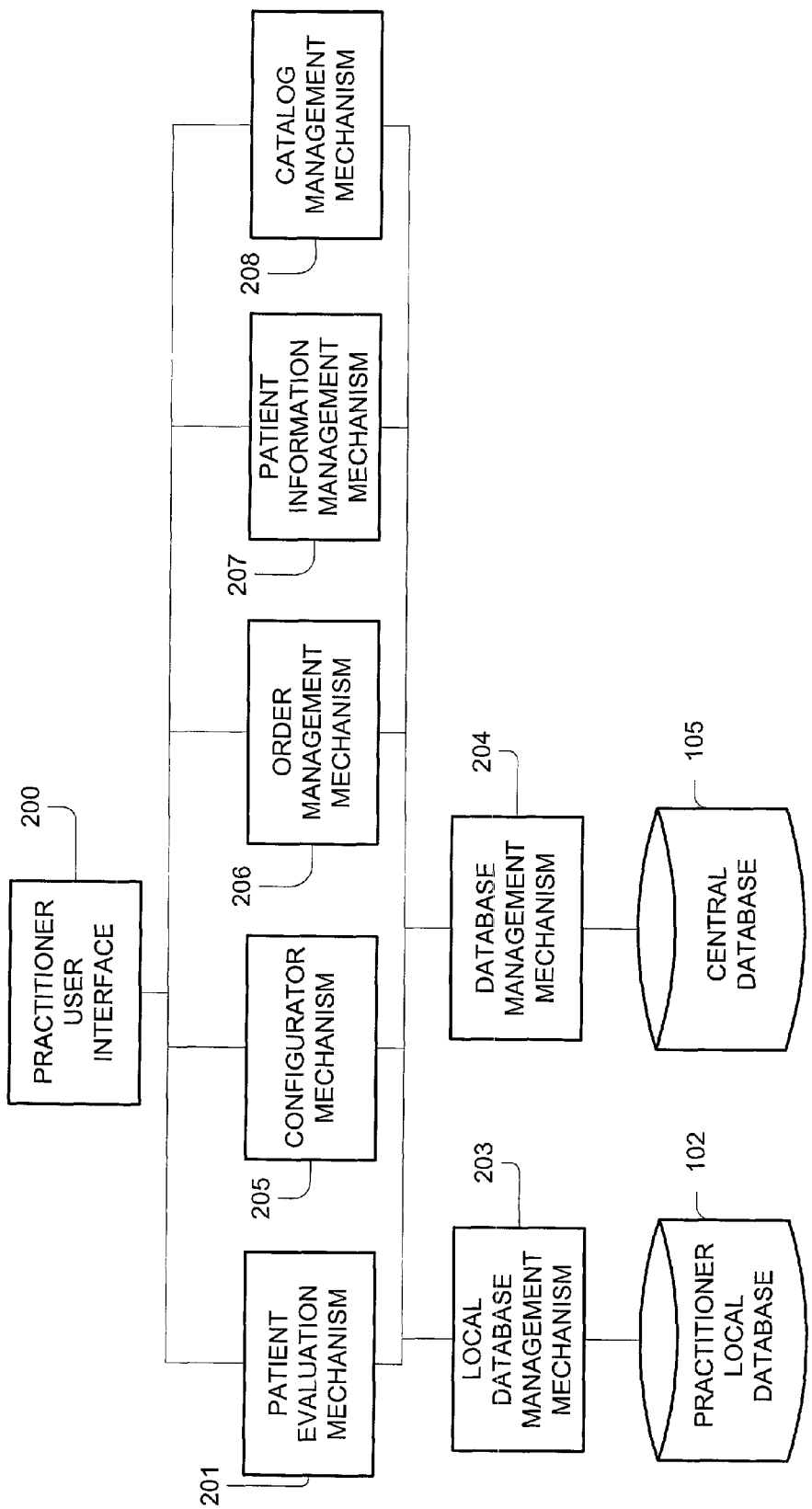
FIG. 2 is a block diagram showing mechanisms of the personal data assistant, practitioner workstation, and web server of FIG. 1 according to one embodiment of the present invention.

FIG. 2 shows the mechanisms implemented by the PDA 100, the practitioner workstation 101, and the web server 104 according to one embodiment of the present invention. The practitioner user interface 200 provides an interface through which a practitioner may enter patient information as well as interact with the other mechanisms. As discussed above, the practitioner user interface 200 may run on either a PDA 100, or the practitioner workstation 101, or other device that can support an interactive user interface. In one embodiment of the present invention, the practitioner user interface is a web-based interface implemented in a standard markup language such as, for example, HTML, DHTML, XML, WML, or HDML.

The patient evaluation mechanism 201 interacts with the central database 105 through the database management mechanism 204. The patient evaluation mechanism 201 serves as a conduit between the practitioner interacting with the practitioner user interface 200 and the central database 105. The patient evaluation mechanism 201 is also configured to receive input data from external devices, such as a digitizer 106, a digital camera 107, and/or a digital video camera 108, and to store that information in an acceptable format in the central database 105 via the database management mechanism 204. The patient evaluation mechanism 201 ensures that the appropriate patient information is gathered for a particular patient. For example, the patient's weight, height, size, shape, and clearance of a residual limb, the size and shape of a contralateral limb, the size and shape of a limb for which an orthotic device is to be configured, and the patient's activity level will be used by the configurator mechanism 205 to configure three options for a medical device meeting the particular patient's needs.

The database management mechanism 204, as discussed above, provides a mechanism through which all other mechanisms may interact with the central database 105. The database management mechanism is bi-directional, in that information being stored in and retrieved from the central database 105, does so through the database management mechanism 204.

The local database management mechanism 203 provides a function similar to that of the database management mechanism 204, but in relation to the practitioner local database 102. Information gathered by the patient evaluation mechanism 201 may be stored in the practitioner local database 102 via the local database management mechanism 203. Information stored locally in the practitioner local database 102 may be later transferred or copied to the central database 105.

Patient-specific information is stored in the practitioner local database 102 and the central database 105 with a patient-unique identification indicator. The databases associate not only the patient's personal information with the patient-unique identification indicator, but also information related to the medical device or components purchased for the patient, as well as other information, including, but not limited to, insurance reimbursement information (e.g., carrier information, L code information, etc.), account information, and so forth. Maintaining this information allows the vendor to keep a record of which components were given to a particular patient (e.g., by storing component serial numbers associated with the patient to which they were sold), and allows the practitioner to maintain patient history, and to integrate the system of the present invention with other systems used in running the practitioner's practice (e.g., a patient management system, a billing system, an insurance reimbursement system, etc.).

The practitioner user interface 200 further provides a mechanism through which a practitioner may interact with the configurator mechanism 205, the order management mechanism 206, the patient information management mechanism 207, and the catalog management mechanism 208. The configurator mechanism 205 is used to configure medical device systems based on patient evaluation information stored in the central database 105 by the patient evaluation mechanism 201. The configurator mechanism 205 interacts with patient evaluation information stored in the central database 105 through the database management mechanism 204. In one embodiment of the present invention, the configurator mechanism 205 creates three optional medical device configurations based on the patient evaluation information stored in the central database 105. These three options are presented to the practitioner via the practitioner user interface 200. The practitioner may then interact with the configurator mechanism 205 via the practitioner user interface 200 in order to customize, or otherwise manipulate the proposed optional prosthetic configurations.

Once the practitioner has configured a medical device to his or her satisfaction, that information is stored in the central database 105 by the configurator mechanism 205 through the database management mechanism 204. Information is stored in the central database 105 based on which practitioner, and which patient of that practitioner, the information pertains. The patient information management mechanism 207 provides a mechanism through which the practitioner user interface 200 may query and maintain patient-specific information in the practitioner local database 102 or the central database 105. The patient information management mechanism 207 includes processes for maintaining L-code information for patients, generating letters of necessity for patients, and for querying the practitioner local database 102 or the central database 105 for patient-specific information. The processes of the of the patient information management mechanism are accessible via a "my space" capability of the practitioner user interface 200. The "my space" capability provides a mechanism through which a particular practitioner may access all information pertaining to all of their patients. The "my space" capability of the practitioner user interface 200 enables quick access to all information regarding their particular patients and their order history. The "my space" portion of the practitioner user interface 200 also provides status information, including tracking information, for all pending orders placed by the practitioner.

The order management mechanism 206 provides the ability to order either individual components from a catalog maintained within the central database 105, or a "package" of components making up a system configuration stored in the central database 105 as customized by a practitioner through the configurator mechanism 205. The practitioner may interact with the order management mechanism 206 via the practitioner user interface 200 (e.g., via the "my space" capability). In one embodiment of the present invention, the order management mechanism 206 is configured to allow order entry as well as status checking and package tracking for orders placed.

The catalog management mechanism 208 is available via the practitioner user interface 200 and provides a mechanism through which a practitioner may browse a catalog of all available components maintained within the central database 105. In one embodiment of the present invention, the catalog management mechanism 208 provides the ability to search for, browse, and access product information on all medical device components that are maintained within the central database 105.

FIG. 3 is a flow diagram illustrating a process through which a medical device satisfying a particular patient's needs is configured and ordered according to one embodiment of the present invention. As shown in FIG. 3, the process begins at step S301 where the practitioner interviews the patient. As discussed above, the practitioner can collect the patient information by interacting with the practitioner user interface 200 via a personal data assistant 100. The interview process includes asking the patient a list of predetermined main screening questions that are customized to the type of medical device being configured. For example, if the patient is being interviewed for having a lower extremity prosthetic device configured for them, the main screening questions are used to determine information such as the amputation level, the clearance distance between the stump and the ground, the activity level of the patient, the patient's weight, and the desired suspension system for the prosthetic device. Similar sets of questions are asked for other medical devices that may be configured using the system of the present invention, including, but not limited to upper extremity prosthetics, lower extremity orthotics, upper extremity orthotics, and spinal orthotics. Of course, the list of main screening questions for a particular medical device may vary based on the particular implementation of the system of the present invention.

After the patient has been interviewed, the process proceeds to step S302 where it is determined which component classes are required for the patient's prosthetic device. The component classes correspond to the major components of a medical device. Examples of component classes, as shown in Table 1 below, for a lower extremity prosthesis include, but are not limited to, foot, ankle, knee, liner, suspension system, and cosmesis. Examples of component classes for other types of medical devices are also included in Table 1 below:

TABLE 1

Examples of Component Classes for Various Medical Devices

| Lower Extremity Prosthetics | Upper Extremity Prosthetics | Lower Extremity Orthotics | Upper Extremity Orthotics | Spinal Orthotics |
|---|---|---|---|---|
| Foot | Terminal Device (s) | Foot | Finger | Neck |
| Ankle | Wrist | Ankle | Wrist | Back |
| Knee | Elbow | Knee | Elbow | Pelvis |
| Hip | Shoulder | Hip | Shoulder | etc. |
| Liner | Liner | etc. | etc. | |
| Suspension | Suspension | | | |
| Cosmesis | Cosmesis | | | |
| etc. | etc. | | | |

The determination as to which component classes are required is directly derivable from the patient's answers to one or more of the main screening questions. For example, if the patient interview determined that the amputation level of a prosthetic patient was below the knee, it would follow that a knee would not be a required component class for this patient.

Once it is determined which component classes are required for a particular patient, the process proceeds to step S303 where the system determines which products stored in the central database 105 are available for each of those required component classes. Other criteria from the patient's answers to the main screening questions are applied in making a determination as to which products for each required component class satisfy the particular patient's needs. As an example of how this determination is made, stored with each product in the central database 105 is information from which the applicability of a particular product for a particular patient may be determined. For example, stored with each component is an activity level indicator that specifies a maximum patient activity level on a scale of 1 to 4 for which that component may be used. Accordingly, if a patient indicates in the patient interview that they have an activity level of 3, only those components supporting activity levels 3 or 4 are candidates for this particular patient.

The process then proceeds to step S304 where a ranking criteria is applied to the lists of products meeting the patient's requirements. Examples of ranking criteria include, but are not limited to, cost, weight, height, width, functionality, and inventory level. After each of the products meeting the patient's criteria is ranked, the process proceeds to step S305 where a ranked list of medical devices satisfying this particular patient's needs is proposed. The ranked list of medical devices includes components from each of the required component classes. By ranking the medical devices, a "good," "better," and "best" medical device may be presented to the practitioner.

Once the ranked list of medical devices has been proposed, the process proceeds to step S306 where the practitioner selects one of the proposed medical devices and customizes it to further refine the medical device for this particular patient. In this step, further information determined during the patient interview may be used to pre-populate options for the selected medical device. For example, information such as foot size, foot side, heel height, and toe stiffness of a prosthetic patient may be pre-populated for the practitioner based on information determined during the patient interview. As discussed above, different questions are asked of the patient based on the type of device being configured. Once the customization has been completed, the process proceeds to step S307 where the practitioner places an order for the customized proposed medical device.

FIG. 4 is a block diagram illustrating one exemplary use of the system of the present invention for configuring and purchasing a medical device. As shown in FIG. 4, patient information 401 is stored in the central database 105. The configurator 402 accesses the patient information 401 from the central database 105. As discussed above, the configurator 402 uses the patient information 401 to arrive at three medical device options, medical device option one 403, medical device option two 404, and medical device option three 405. These three options provide tailored solutions for the patient based on the patient information 401 acquired during the patient interview, and further provide three different configurations from which to choose. For example, medical device option one 403 may be categorized as a "good" option, while medical device option two 404 may be categorized as a "better" option, and medical device option three 405 may be categorized as the "best" option. The "good," "better," and "best" options, as an example, may have an associated low, medium, and high price, respectively. As discussed above, the ranking of the three options need not be only based on cost, but could also be based on weight, height, width, inventory, or other criteria.

In one embodiment of the present invention, the three proposed medical device options 403, 404, 405 are selected from a larger number of available medical device configurations that are stored in the central database 105. Based on the patient information 401, the configurator 402 selects the three medical device options 403, 404, 405 based on criteria related to the patient information 401.

Each of the three medical device options 403, 404, 405 includes components from each of the component classes required, as determined from the patient interview. The practitioner user interface 200 allows the practitioner to select one of the proposed medical device options as the selected device for the patient. The practitioner may then use the customizer 407 to customize the selected medical device option, and order that customized version. The customization process includes further defining the exact medical device for a patient. This further definition of the medical device includes adding details dependent on the type of medical device being configured including, but not limited to, left side or right side components, size (e.g., foot size), stiffness, alignment, padding, cosmesis, and color. Some of the information required for the customization is available from the patient interview, in which case the customizer 407 pre-populates the values from data stored in the central database 105 during the patient interview process.

In one embodiment of the present invention, the results of the customization are stored in the central database 105 and used to provide feedback for adjusting the algorithms applied by the configurator 402. In one embodiment of the present invention, artificial intelligence techniques known to those of ordinary skill in the artificial intelligence software art are used to identify trends regarding the acceptance and rejection of the medical device options 403, 404, 405 selected by the configurator 402 based on the patient information 401.

For example, a particular component 'X' of medical device may be identified by an algorithm of the configurator 402 as being a desirable component associated with a patient having attribute '1.' In practice, though, each time a practitioner selects a medical device including component 'X,' the practitioner uses the customizer 407 to change component 'X' to component 'Y.' This trend information (i.e., the results of the customizations) is stored in the central database 105, and artificial intelligence techniques are applied to use this information to adjust the algorithm of the configurator 402 to cause component 'Y' to be selected for patients having attribute '1' in the future. This feedback mechanism is an ongoing process through which the algorithms determining the proposed medical devices are refined to "learn" from historical information.

FIG. 4A is a flow diagram illustrating a process through which an algorithm for configuring a medical device is adjusted according to one embodiment of the present invention. As shown in FIG. 4A, the process begins at step S401 where an algorithm is developed to propose a medical device based on patient information 401. The process then proceeds to step S402 where the algorithm is applied to propose a medical device for a particular patient based on patient information 401. The process then proceeds to step S403 where it is determined whether the proposed medical device was purchased as proposed or customized. If it is determined that the proposed medical device was not customized (i.e., "No" at step S403), the process proceeds to step S404 where it is determined to continue using the existing algorithm.

If, on the other hand, it is determined that the proposed medical device was customized prior to being purchased (i.e., "Yes" at step S403), the process proceeds to step S405 where the results of that customization are stored in the central database 105. The process then proceeds to step S406 where a determination is made as to whether a trend has developed regarding the customization of a particular proposed medical device. As discussed above, this trend may indicate, among other things, that a particular component of a proposed medical device is consistently de-selected during a customization process. If it is determined that no trend has developed in the customization of proposed medical devices (i.e., "No" at step S406), the process proceeds to step S404 where a determination is made to continue using the existing algorithm.

If, on the other hand, a trend is uncovered (i.e., "Yes" at step S406), the process proceeds to step S407 where the existing algorithm is adjusted to accommodate the trend discovered at step S406. As described above, the discovery of the trend, as well as the adjustment to the algorithm may be implemented using known artificial intelligence techniques. The process then proceeds to step S408 where the existing algorithm is replaced by the new, adjusted algorithm. The process then proceeds to step S402 where the new algorithm is applied to propose a medical device. As indicated by the flow of the process shown in FIG. 4A, the adjustment and "learning" process is an ongoing process through which an algorithm may be refined. As would be understood by one of ordinary skill in the software art, the techniques illustrated in FIG. 4A and described above are equally applicable to other algorithms of the present invention.

Returning to FIG. 4, in this example, the practitioner has used the customizer 407 to customize medical device option one 403. After the option has been customized, the customized version of medical device option one 403A is displayed to the user on a summary page 408 so that the customizations may be reviewed prior to placing an order. If the customized version of medical device option one 403A is satisfactory to the practitioner, the medical device is ordered by placing it into the shopping cart 406. By having the ability to customize a particular medical device option, the practitioner has the ability to apply his unique skills in configuring the best solution for his particular patient. Moreover, since many prosthetists, for example, have favored approaches for interfacing and connecting prosthetic components, the configurator provides the prosthetist the option of de-selecting all connectors and interfaces available for a particular option. As recognized by the present inventors, this ability allows practitioners to apply their skills in arriving at the best solution for the patient.

All information pertaining to the ordered medical device is maintained in the central database 105, and may be accessed by the practitioner through the "my space" capability provided by the practitioner user interface 200. The information maintained in the central database 105 is related to the particular patient for which the medical device was ordered.

Figure 5:
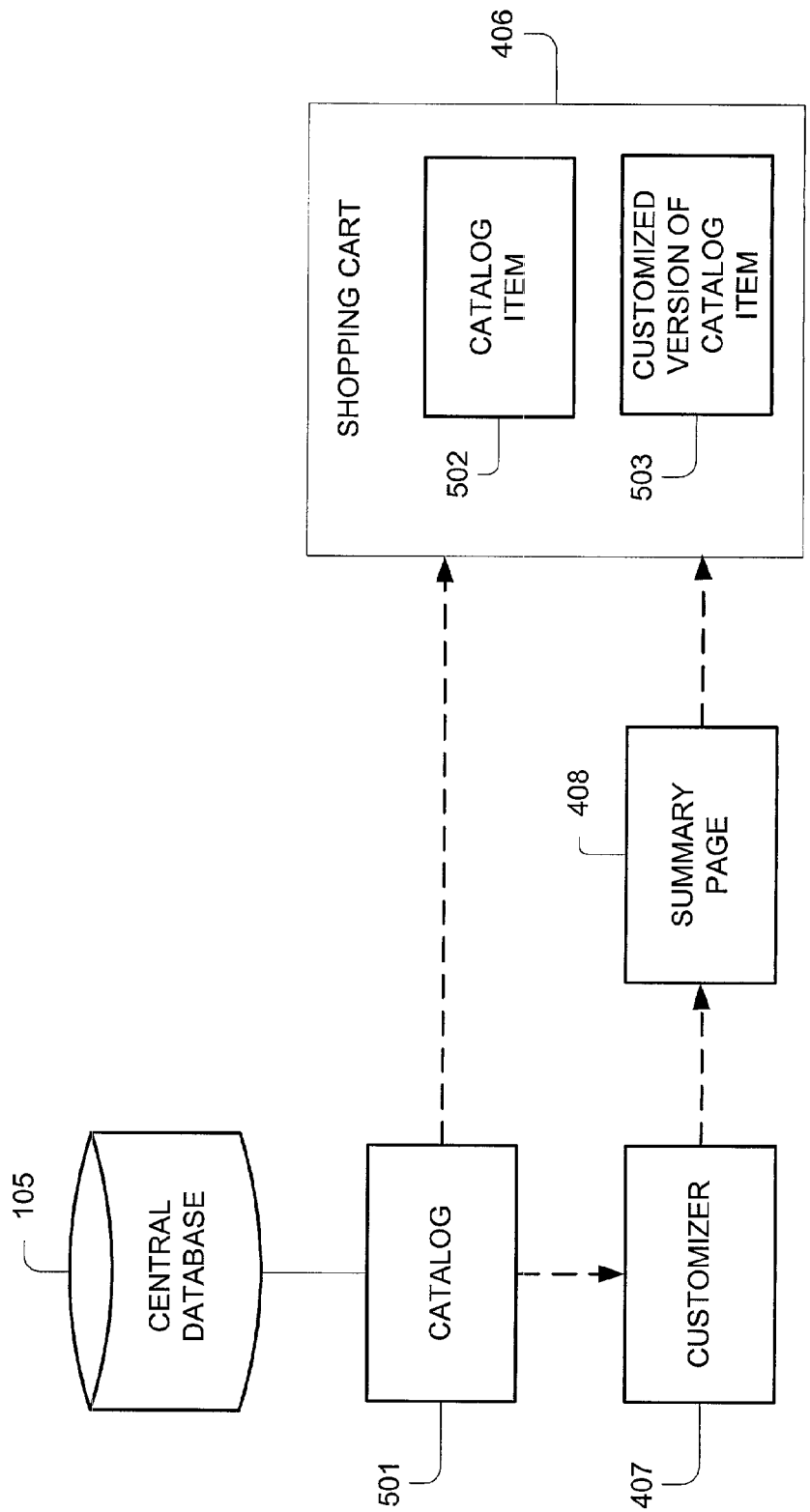
FIG. 5 is a block diagram showing the ordering of a catalog item and a customized version of a catalog item according to one embodiment of the present invention.

FIG. 5 is a block diagram illustrating another exemplary use of the system of the present invention for purchasing medical device components. As shown in FIG. 5, the system includes a catalog 501 of the various medical device components maintained in the central database 105. The catalog 501 is accessible through the practitioner user interface 200. Once the desired items have been selected, they can either be placed directly into the shopping cart 406, or they can be customized using the customizer 407. The shopping cart 406 shown in FIG. 5 illustrates an example where a catalog item 502 was placed directly into the shopping cart 406 from the catalog, and a customized version of a catalog item 503 that was placed into the shopping cart 406 after having been customized via the customizer 407. For catalog items that are customized by the customizer 407, the customized version of the catalog item is displayed to the user on a summary page 408 so that the customizations may be reviewed prior to placing an order. If the customized version of the catalog item 503 is satisfactory to the practitioner, the medical device is ordered by placing it into the shopping cart 406.

Figure 6:
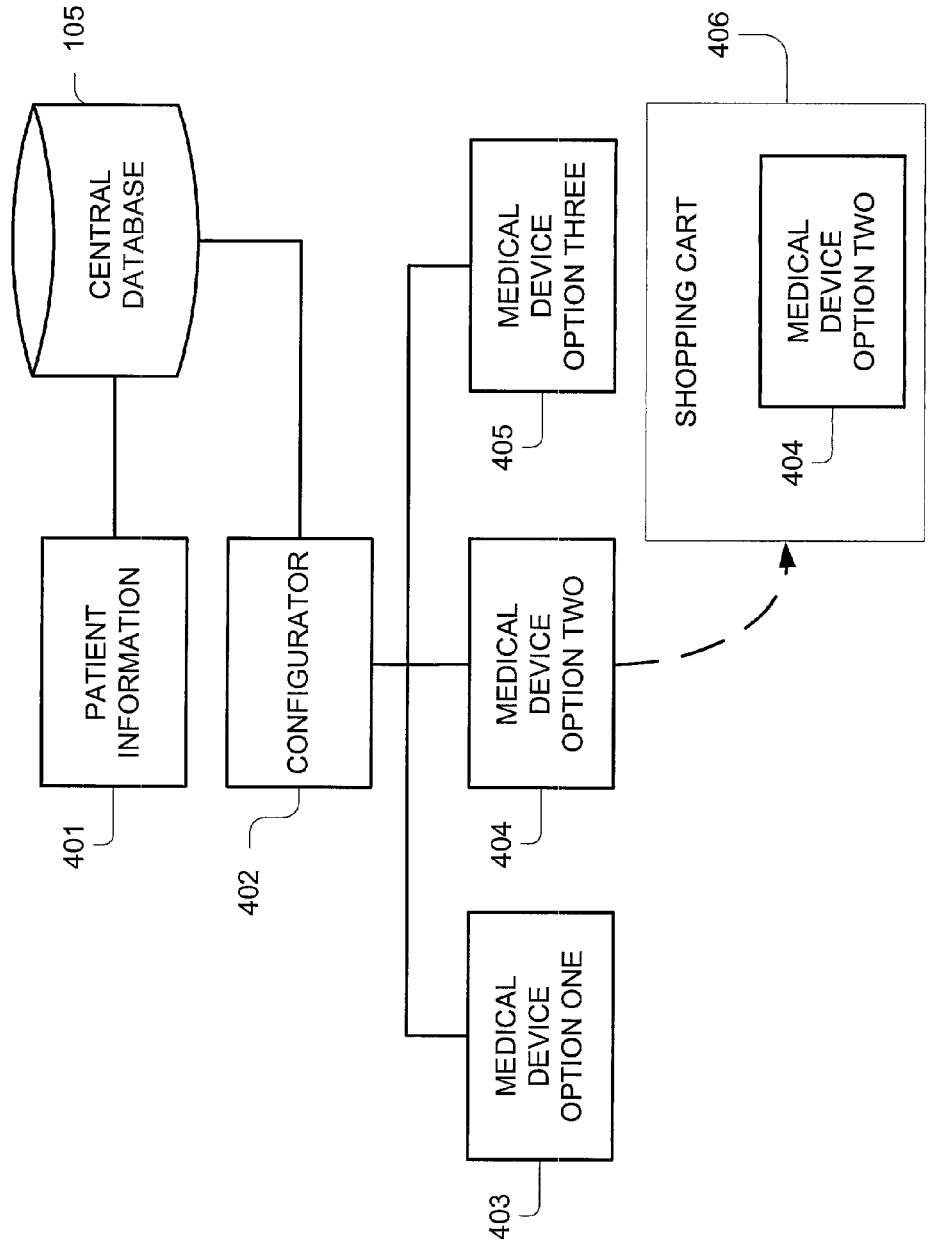
FIG. 6 is a block diagram illustrating the presentment of three options based on input patient information, and the ordering of one of those options according to one embodiment of the present invention.

FIG. 6 is a block diagram illustrating yet another exemplary use of the system for purchasing a medical device. As shown in FIG. 6, this use of the system of the present invention includes purchasing one of the three medical device options 403, 404, 405 as configured by the configurator 402, without first customizing the selected option using the customizer 407. In this example, once the three medical device options 403, 404, 405 are generated, the practitioner simply selects one of those options and places it in the shopping cart 406. In the example shown in FIG. 6, medical device option 2, 404, has been selected by the practitioner and placed into the shopping cart 406.

Figure 7:
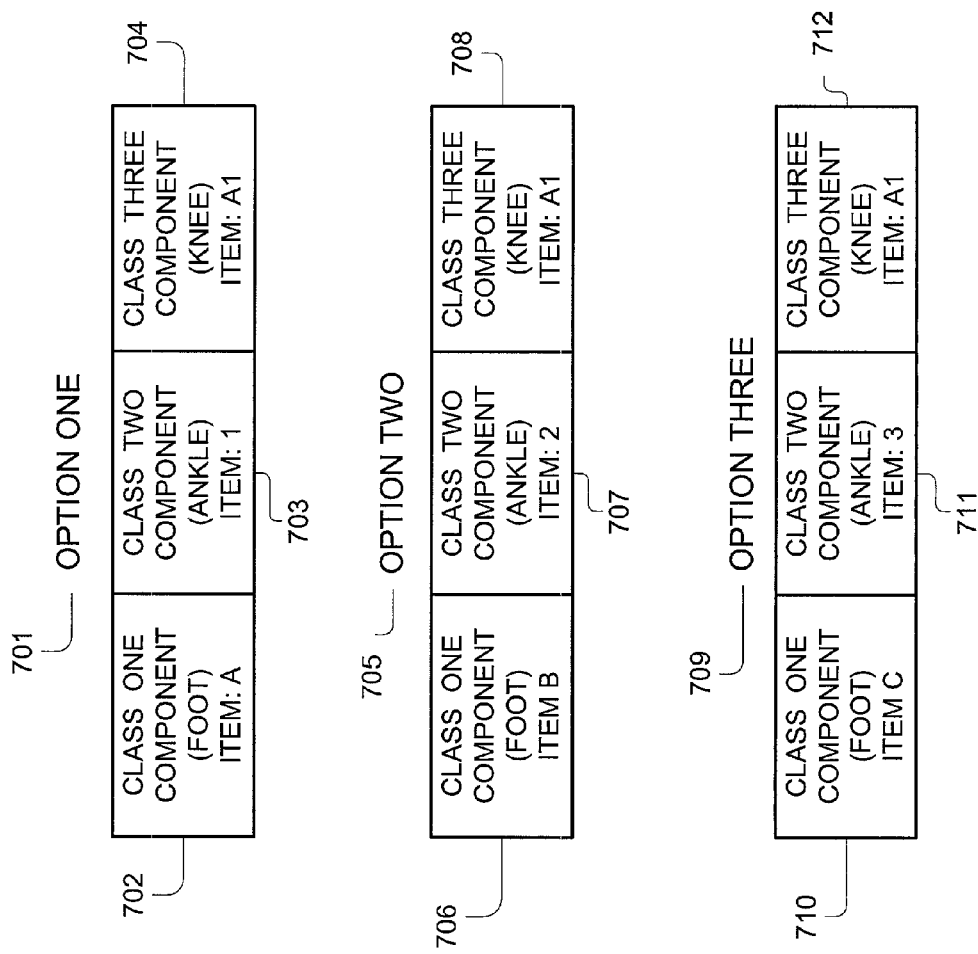
FIG. 7 illustrates exemplary data structures containing information corresponding to each of three medical device options according to one embodiment of the present invention.

FIG. 7 illustrates exemplary data structures in which the various options shown in FIG. 4 and FIG. 6 may be stored in the central database 105. As shown in FIG. 7, option one 701, option two 705, and option three 709, each include three fields. Each option includes a class one component 702, 706, 710, a class two component 703, 707, 711, and a class three component 704, 708, 712. In this example, the combination of a class one component, a class two component, and a class three component provide a complete prosthesis option for this particular exemplary patient. In other examples, the fields would include class components required for an upper extremity prosthetic, a lower extremity orthotic, an upper extremity orthotic, a spinal orthotic, or another type of medical device. In the example of FIG. 7, if a class one component corresponds to a foot, a class two component corresponds to an ankle, and a class three component corresponds to a knee, each of these options would be a viable prosthesis option for an above-the-knee amputee. As further illustrated in FIG. 7, while option one 701, option two 705, and option three 709 all include the same component parts, none of the options are identical. For example, option one 701 includes foot A, ankle 1, and knee A1. Option two includes foot B, ankle 2, and knee A1. Option three includes foot C, ankle 3, and knee A1. While all three options include the same class three component (i.e., knee A1), none of the options have the same class one component, class two component combination. Based on information stored in the central database 105, it is possible for the configurator 402 to categorize each of these three options as "good," "better," and "best."

FIG. 8 illustrates exemplary data structures showing information stored with the various medical device components within the central database 105. FIG. 8 illustrates the different information that may be stored with each of the different foot options available for a particular prosthetic device. FIG. 8 shows five records 801, each of which corresponds to a different foot option. Each record includes a component identification field 802, a field indicating the maximum patient weight that may be supported by the foot 803, a field indicating the maximum activity level that can be supported by the particular foot 804, a price field 805, and a component weight field 806. The configurator 402 uses the information in the various fields in arriving at the three proposed options. For example, based on the patient interview information, the configurator 402 may determine, for example, based on a particular patient's weight, that a particular foot is not an option for this patient. For example, if it was determined during the patient interview that a patient weighs 250 lbs., based on information stored in the foot records 801, a decision is made by the configurator 402 that foot A, foot B, foot D, and foot E are not acceptable options for this patient. Accordingly, in this example, only foot C would be viable for this patient. Similarly, the configurator 402 may use information stored in the other fields of the records 801 in configuring options. FIG. 8 illustrates but one example of the types of information that may be stored with the various medical device components. As would be understood by one of ordinary skill in the art, the configurator 402 can include processing to arrive at medical device options using a variety of different information, which could be stored with each of the various component types.

The price field 805 stored with each record 801 is used by the configurator 402, along with corresponding price fields of the other components included in the medical device option, in determining a total price for each of the medical device options, medical device option 1, 403, medical device option 2, 404, and medical device option 3, 405. Moreover, the configurator 402 can access information stored in the component weight field 806 to determine a total weight for a particular option. Summary-type information pertaining to the various medical device options will be presented to the practitioner on the summary page 408 following the customization of an option with the customizer 407. By presenting the summary information on the summary page 408, the practitioner is able to reconsider the modifications made during the customization process.

Figure 9:
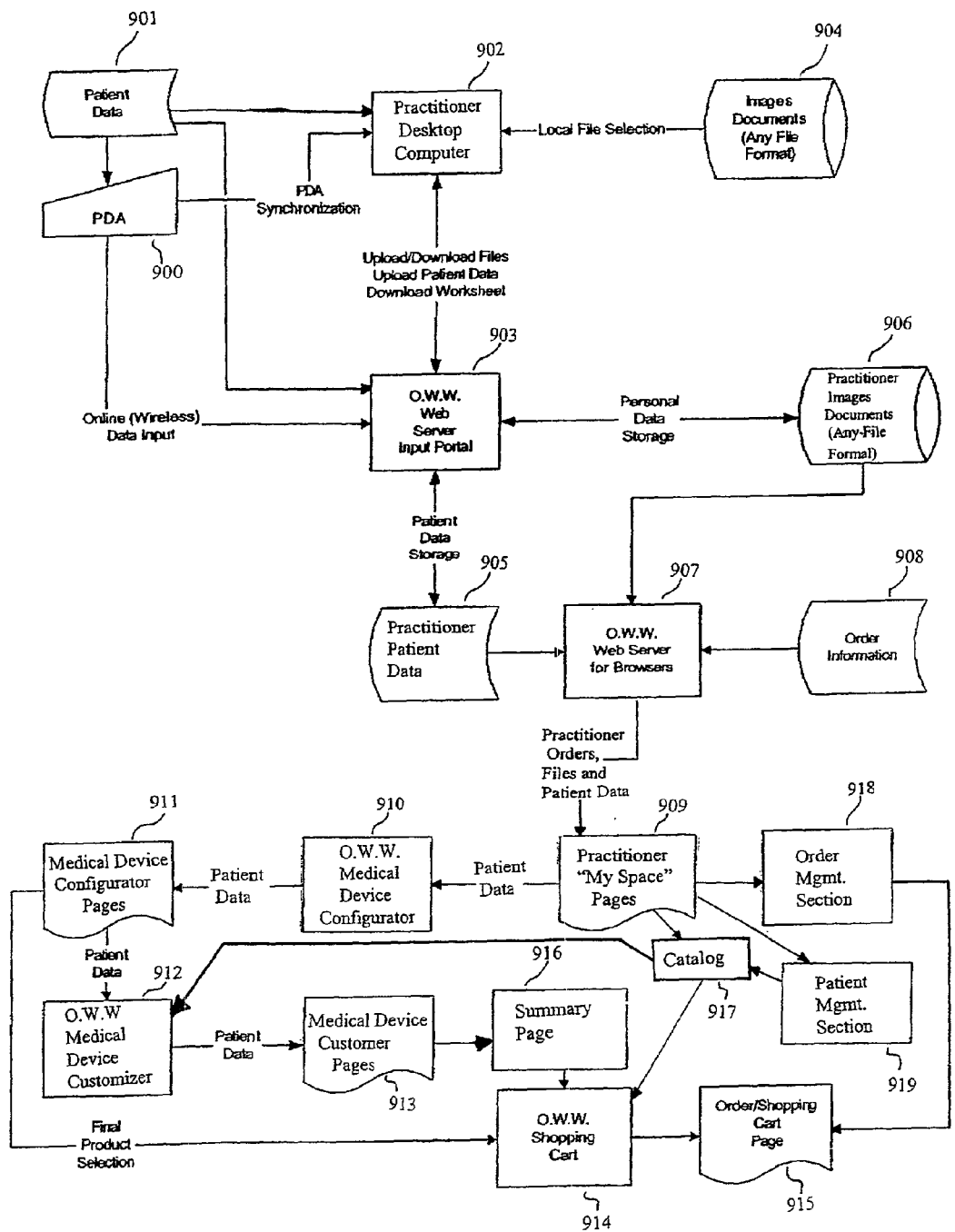
FIG. 9 is an overall system flow diagram according to one embodiment of the present invention.

FIG. 9 illustrates an overall system flow according to one embodiment of the present invention. As shown in FIG. 9, a practitioner uses a PDA 900 to input patient data 901 relating to the patient's physical and lifestyle characteristics. In other embodiments, the patient data 901 is input directly into the practitioner desktop computer 902, or input via the web server input portal 903. The patient data 901 may be stored on the practitioner desktop computer 902 through a common PDA synchronization. The practitioner desktop computer 902 may also import images or other documents from any acceptable data source 904. Alternatively, the patient data 901 may be transmitted to the web server input portal 903 via a wireless connection. If the patient data 901 was stored on the practitioner desktop computer 902, that information may also be uploaded or downloaded from the web server input portal 903 along with any other images or documents 904 stored on the practitioner desktop computer 902.

The web server input portal 903 provides a personal data storage area for the practitioner in which practitioner-specific documents may be stored 906. The patient data 901 provided to the web server input portal 903 are also stored in a patient-specific data area 905.

Through a browser running on the practitioner desktop computer 902 or on the PDA 900, the practitioner can access the web server 907. The web server 907 provides a user interface that allows the practitioner to log in to the system and thereby access data related to their patients and their historical order information 908. Patient-specific data 905 may be accessed through practitioner "My Space" pages 909 for configuring a medical device. The medical device configurator 910 receives the patient data and presents medical device options to the practitioner through the medical device configurator pages 911. The practitioner may customize one of the medical device options by selecting that option from the medical device configurator pages 911 and processing it with the medical device customizer 912. The medical device customizer pages 913 allow the practitioner to access the functionality of the medical device customizer 912 to customize a medical device solution. Once a customized option has been completed, the practitioner will have the customized option presented in the summary page 916 so that a review of the customizations can be done. The customized option may then be ordered by placing it in the shopping cart 914. The practitioner "My Space" pages 909 provide access to both historical and current order status information through the order management section 918.

In an alternative embodiment, the practitioner can select one of the medical device configurations presented on the medical device configurator pages 911 and place it directly into the shopping cart 914 without performing the customization process described above.

The practitioner "My Space" pages 909 also provide access to a catalog 917 of medical device components. As with the medical device options, the catalog items may also be customized through the customizer 912. When catalog items are customized, the customized version of the catalog item is presented in the summary page 916 prior to ordering. The customized catalog item may then be ordered by placing it in the shopping cart 914. Alternatively, if the catalog item is not customized, the catalog item may be placed directly into the shopping cart 915 without going through the summary page 916.

The practitioner "My Space" pages 909 also provide access to a patient management section 919. The patient management section 919 provides a practitioner with access to patient-specific information such as, for example, patient history information including part numbers of medical devices ordered in the past, reimbursement information, account balance information, and information concerning letters of necessity generated for a particular patient. In one embodiment of the present invention, the patient management section 919 provides access to the catalog 917 thereby facilitating, for example, the order of replacement parts for a medical device of a particular patient.

Figure 10A:
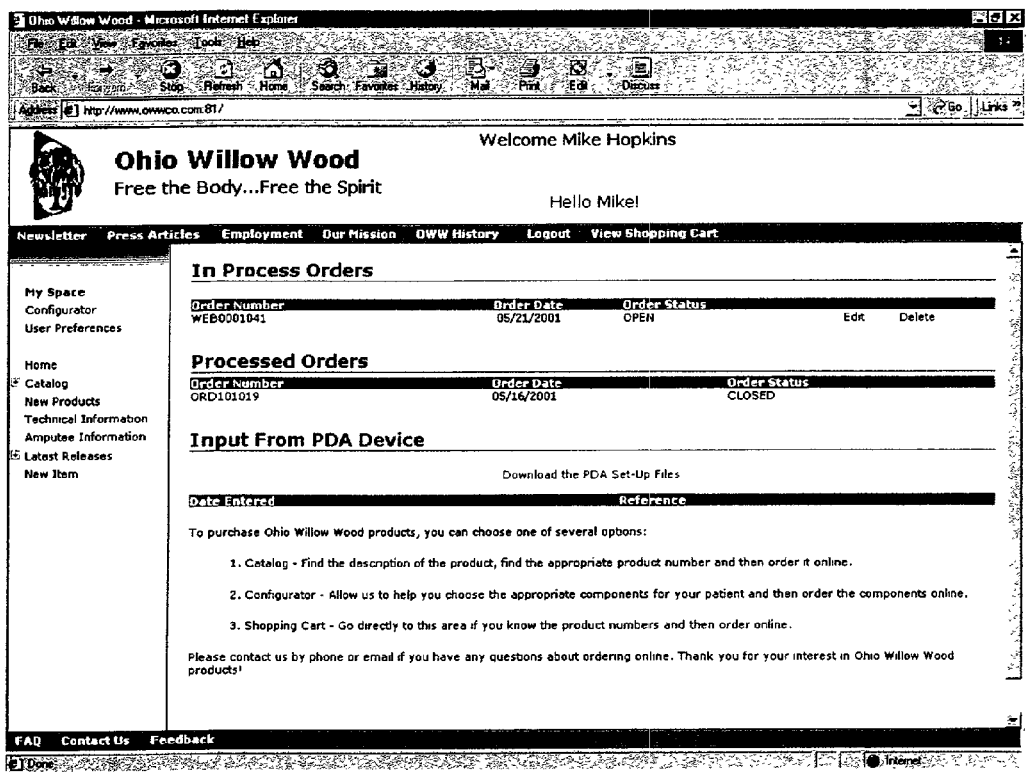

FIGS. 10A-10H illustrate exemplary screens from a practitioner's user interface according to one embodiment of the present invention. FIG. 10A illustrates an exemplary "My Space" page.

Figure 10B:
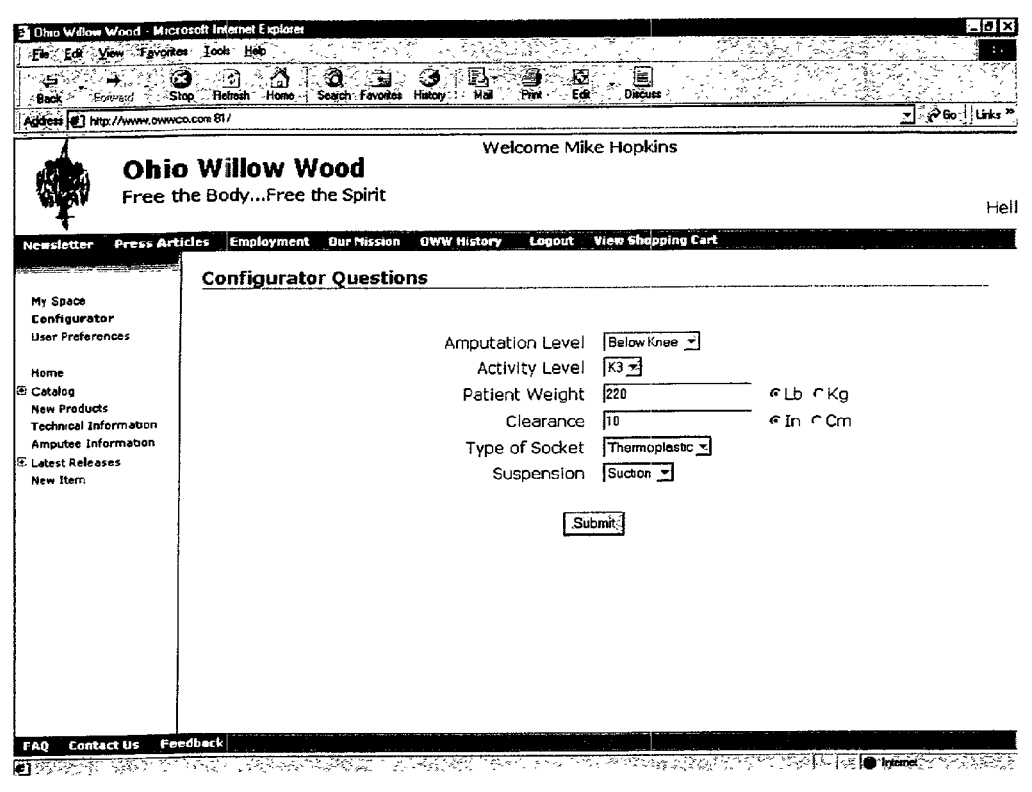

FIG. 10B illustrates an exemplary patient interview screen to be filled out by a practitioner when interviewing a patient for configuring a medical device. In the example shown in FIG. 10B, the questions indicate that the medical device being configured is a lower extremity prosthetic device.

Figure 10C:
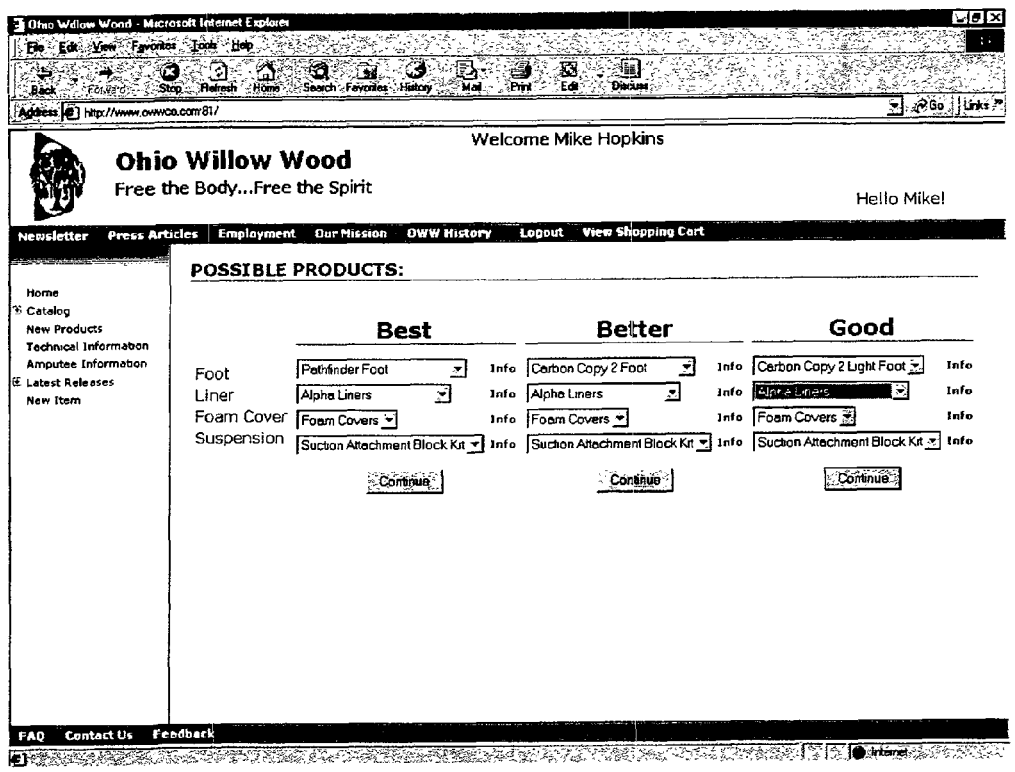

FIG. 10C illustrates an exemplary screen for displaying a "good," "better," and "best" proposed medical device based on a minimal amount of patient information.

Figure 10D:
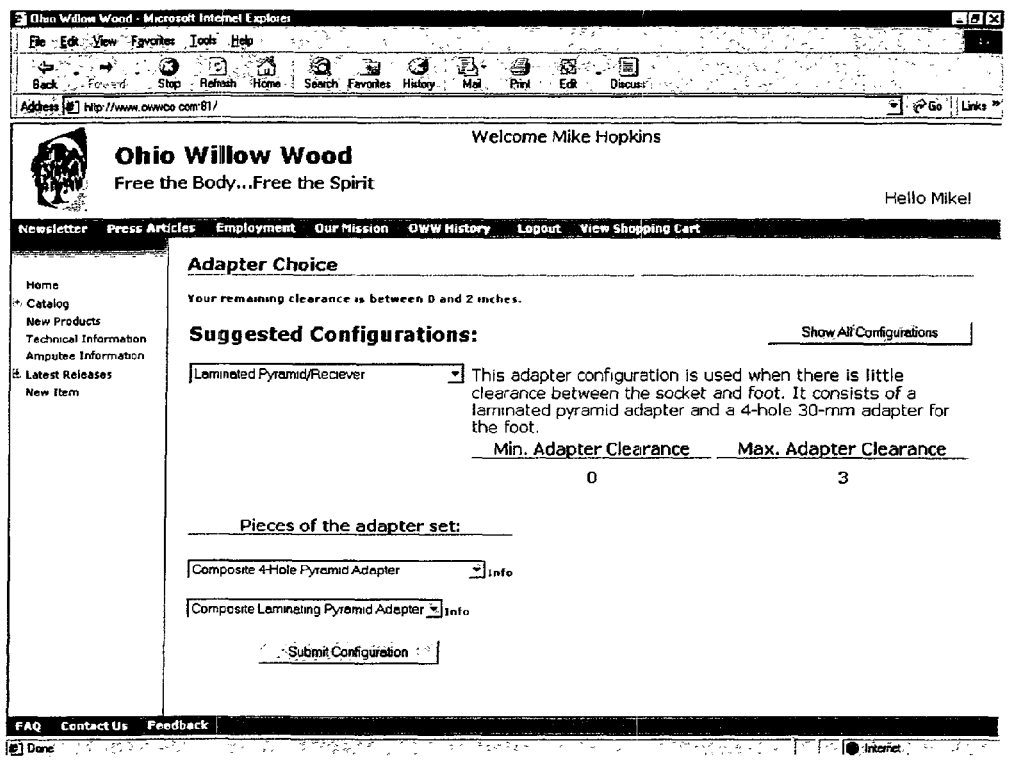

FIG. 10D illustrates an exemplary screen for displaying information about a medical device component from the catalog of components maintained in the central database 105.

Figure 10E:
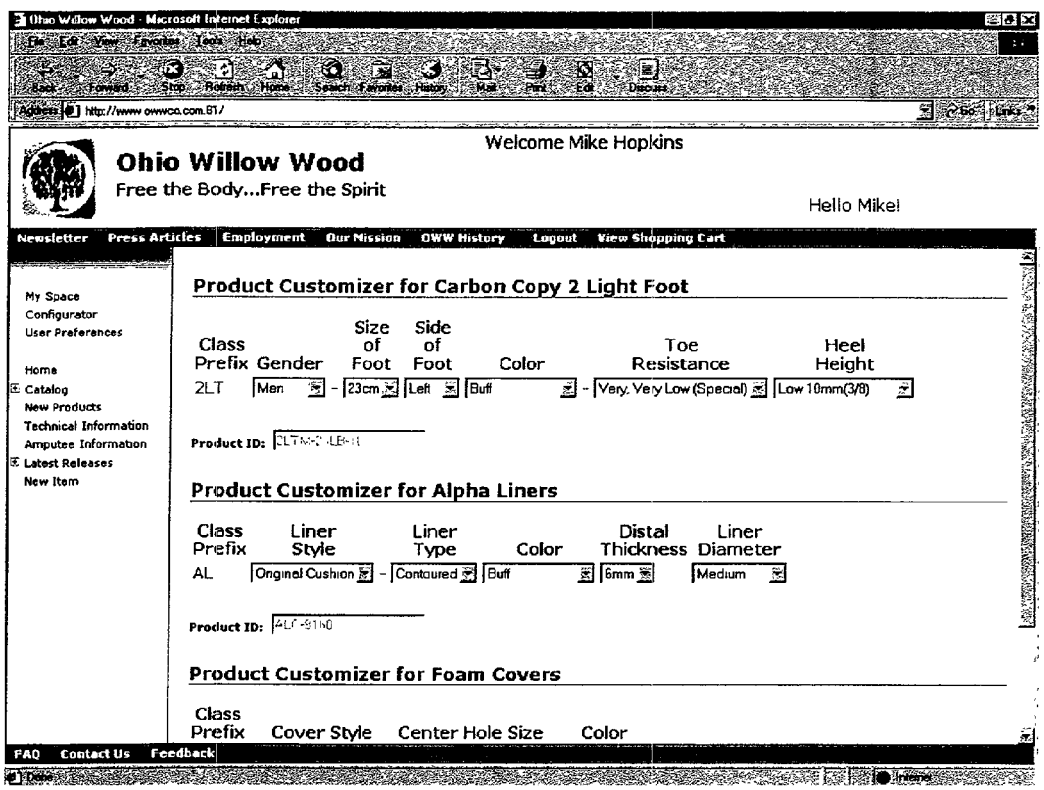

FIG. 10E illustrates an exemplary customizer screen for customizing a selected medical device option.

Figure 10F:
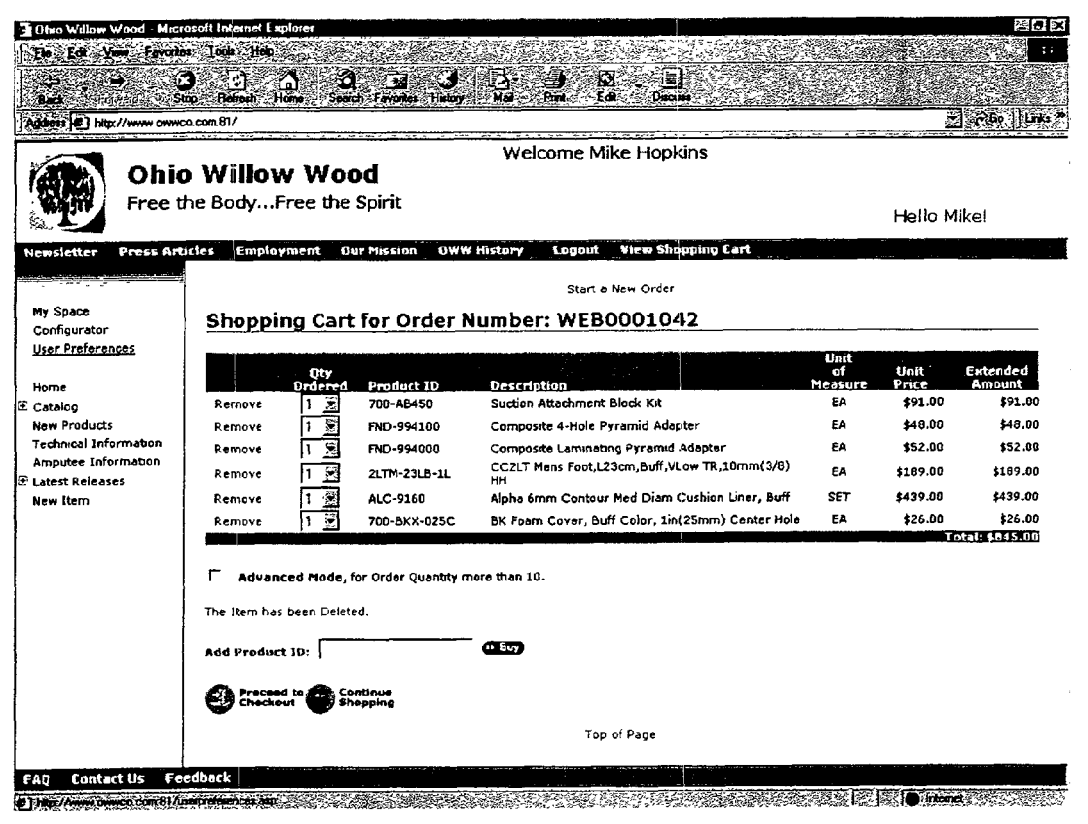

FIG. 10F illustrates an exemplary shopping cart screen indicating the medical device components currently selected.

Figure 10G:
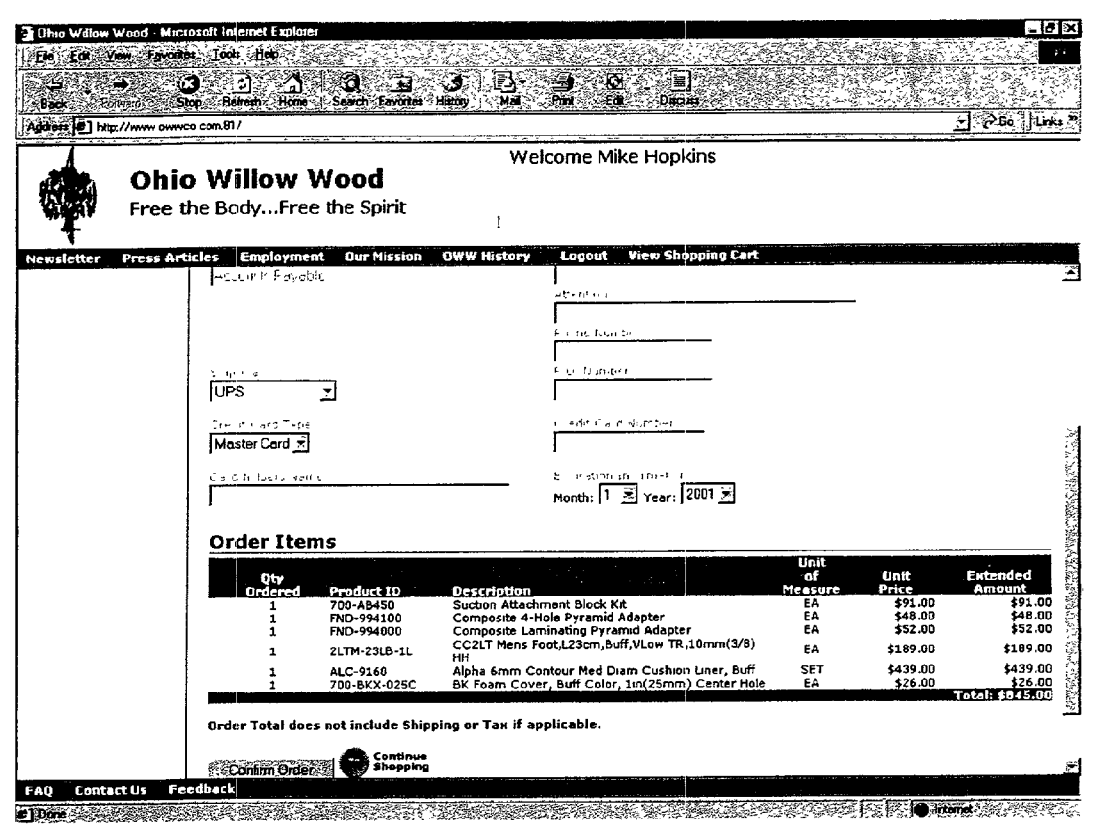

FIG. 10G illustrates an exemplary order form screen for capturing shipping information for an order.

Figure 10H:
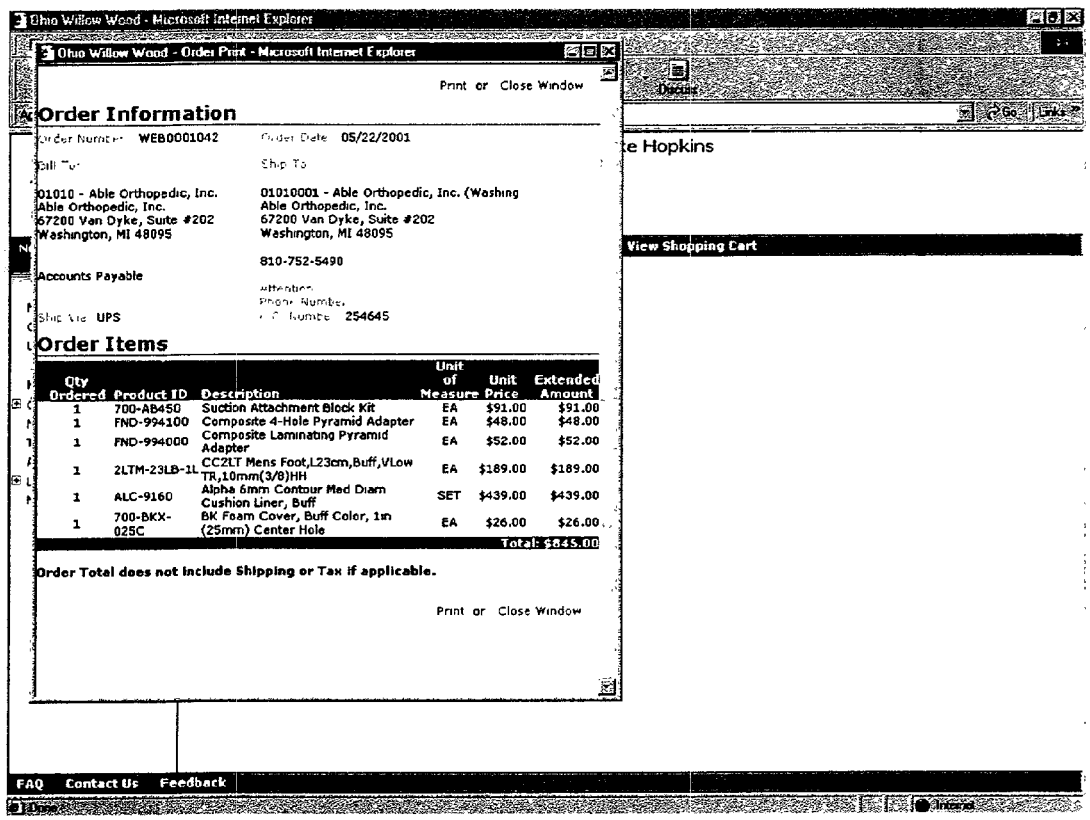

FIG. 10H illustrates an exemplary print order summary screen allowing a practitioner to print a copy of the order being placed.

FIG. 11 illustrates a computer system 1101 upon which an embodiment of the present invention may be implemented. The present invention may be implemented on a single such computer system, or a collection of multiple such computer systems. The computer system 1101 includes a bus 1102 or other communication mechanism for communicating information, and a processor 1103 coupled with the bus 1102 for processing the information. The computer system 1101 also includes a main memory 1104, such as a random access memory (RAM) or other dynamic storage device (e.g., dynamic RAM (DRAM), static RAM (SRAM), and synchronous DRAM (SDRAM)), coupled to the bus 1102 for storing information and instructions to be executed by processor 1103. In addition, the main memory 1104 may be used for storing temporary variables or other intermediate information during the execution of instructions by the processor 1103. The computer system 1101 further includes a read only memory (ROM) 1105 or other static storage device (e.g., programmable ROM (PROM), erasable PROM (EPROM), and electrically erasable PROM (EEPROM)) coupled to the bus 1102 for storing static information and instructions for the processor 1103.

The computer system 1101 also includes a disk controller 1106 coupled to the bus 1102 to control one or more storage devices for storing information and instructions, such as a magnetic hard disk 1107, and a removable media drive 1108 (e.g., floppy disk drive, read-only compact disc drive, read/write compact disc drive, compact disc jukebox, tape drive, and removable magneto-optical drive). The storage devices may be added to the computer system 1101 using an appropriate device interface (e.g., small computer system interface (SCSI), integrated device electronics (IDE), enhanced-IDE (E-IDE), direct memory access (DMA), or ultra-DMA).

The computer system 1101 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1101 may also include a display controller 1109 coupled to the bus 1102 to control a display 1110, such as a cathode ray tube (CRT), for displaying information to a computer user. The computer system includes input devices, such as a keyboard 1111 and a pointing device 1112, for interacting with a computer user and providing information to the processor 1103. The pointing device 1112, for example, may be a mouse, a trackball, or a pointing stick for communicating direction information and command selections to the processor 1103 and for controlling cursor movement on the display 1110. In addition, a printer may provide printed listings of the data structures/information stored and/or generated by the computer system 1101.

The computer system 1101 performs a portion or all of the processing steps of the invention in response to the processor 1103 executing one or more sequences of one or more instructions contained in a memory, such as the main memory 1104. Such instructions may be read into the main memory 1104 from another computer readable medium, such as a hard disk 1107 or a removable media drive 1108. One or more processors in a multi-processing arrangement may also be employed to execute the sequences of instructions contained in main memory 1104. In alternative embodiments, hard-wired circuitry may be used in place of or in combination with software instructions. Thus, embodiments are not limited to any specific combination of hardware circuitry and software.

As stated above, the computer system 1101 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the computer system 1101, for driving a device or devices for implementing the invention, and for enabling the computer system 1101 to interact with a human user (e.g., print production personnel). Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 1103 for execution. A computer readable medium may take many forms, including but not limited to, non-volatile media, volatile media, and transmission media. Non-volatile media includes, for example, optical, magnetic disks, and magneto-optical disks, such as the hard disk 1107 or the removable media drive 1108. Volatile media includes dynamic memory, such as the main memory 1104. Transmission media includes coaxial cables, copper wire and fiber optics, including the wires that make up the bus 1102. Transmission media also may also take the form of acoustic or light waves, such as those generated during radio wave and infrared data communications.

Various forms of computer readable media may be involved in carrying out one or more sequences of one or more instructions to processor 1103 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system 1101 may receive the data on the telephone line and use an infrared transmitter to convert the data to an infrared signal. An infrared detector coupled to the bus 1102 can receive the data carried in the infrared signal and place the data on the bus 1102. The bus 1102 carries the data to the main memory 1104, from which the processor 1103 retrieves and executes the instructions. The instructions received by the main memory 1104 may optionally be stored on storage device 1107 or 1108 either before or after execution by processor 1103.

The computer system 1101 also includes a communication interface 1113 coupled to the bus 1102. The communication interface 1113 provides a two-way data communication coupling to a network link 1114 that is connected to, for example, a local area network (LAN) 1115, or to another communications network 1116 such as the Internet. For example, the communication interface 1113 may be a network interface card to attach to any packet switched LAN. As another example, the communication interface 1113 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1113 sends and receives electrical, electromagnetic or optical signals that carry digital data streams representing various types of information.

The network link 1114 typically provides data communication through one or more networks to other data devices. For example, the network link 1114 may provide a connection to another computer through a local network 1115 (e.g., a LAN) or through equipment operated by a service provider, which provides communication services through a communications network 1116. In preferred embodiments, the local network 1115 and the communications network 1116 preferably use electrical, electromagnetic, or optical signals that carry digital data streams. The signals through the various networks and the signals on the network link 1114 and through the communication interface 1113, which carry the digital data to and from the computer system 1101, are exemplary forms of carrier waves transporting the information. The computer system 1101 can transmit and receive data, including program code, through the network(s) 1115 and 1116, the network link 1114 and the communication interface 1113. Moreover, the network link 1114 may provide a connection through a LAN 1115 to a mobile device 1117 such as a personal digital assistant PDA), laptop computer, or cellular telephone. The LAN communications network 1115 and the communications network 1116 both use electrical, electromagnetic or optical signals that carry digital data streams. The signals through the various networks and the signals on the network link 1114 and through the communication interface 1113, which carry the digital data to and from the system 1101, are exemplary forms of carrier waves transporting the information. The computer system 1101 can transmit notifications and receive data, including program code, through the network(s), the network link 1114 and the communication interface 1113.

Obviously, numerous modifications and variations of the present invention are possible in light of the above teachings. It is therefore to be understood that within the scope of the appended claims, the invention may be practiced otherwise than as specifically described herein.

The invention claimed is:

1. A system for configuring a medical device, comprising:
a digital repository populated with entries defining a plurality of medical device components, each entry associated with an individual medical device component and having
a component identification indicator,
a component class indicator, and
at least one patient attribute indicator;
a processor; and
a computer readable medium encoded with processor readable instructions that when executed by the processor implement
a practitioner user interface mechanism configured to provide a practitioner with access to entries in the digital repository via a network and to allow the practitioner to provide at least one patient interview answer indicator,
a patient interview mechanism configured to receive over the network the at least one patient interview answer indicator corresponding to an attribute of a patient and to store the at least one patient interview answer indicator in a memory, and
configurator mechanism configured to select a subset of entries from the digital repository based on the at least one patient interview answer indicator in the memory, the subset of entries including entries corresponding to individual medical device, components that collectively form a medical device meeting a need of the patient.

2. The system of claim 1, wherein the medical device comprises at least one of a lower extremity prosthetic device, an upper extremity prosthetic device, a lower extremity orthotic device, an upper extremity orthotic device, and a spinal orthotic device.

3. The system of claim 1, wherein:
the computer readable medium is further encoded with processor readable instructions that when executed by the processor further implement a customization mechanism configured to at least one of add, remove, and modify at least one entry of the subset of entries selected by the configurator mechanism, and the practitioner user interface mechanism is further configured to provide access to the customization mechanism.

4. The system of claim 3, wherein the practitioner user interface mechanism is further configured to provide a summary page of components customized by the customization mechanism.

5. The system of claim 3, wherein
the customization mechanism is further configured to store a customization result in the digital repository indicating a change made to the subset of entries selected by the configurator mechanism, and
the computer readable medium is further encoded with processor readable instruction is that when executed by the processor further implements an algorithm adjustment mechanism configured to adjust an algorithm of the configurator mechanism based on the customization result stored in the digital repository, the adjustment causing the configurator mechanism to select a different subset of entries based on the at least one patient interview answer indicator.

6. The system of claim 5, wherein the algorithm adjustment mechanism comprises an application of artificial intelligence.

7. The system of claim 1, wherein:
the computer readable medium is further encoded with processor readable instructions that when executed by the processor further implement a medical device shopping mechanism configured to place an order for the medical device and to store order information in the digital repository, and
the practitioner user interface mechanism is further configured to provide access to the medical device shopping mechanism.

8. The system of claim 7, wherein the medical device shopping mechanism is further configured to determine all applicable price discounts for the medical device available to the practitioner.

9. The system of claim 1, wherein at least a portion of the practitioner user interface mechanism is accessible via a personal data assistant.

10. The system of claim 1, wherein at least a portion of the network comprises an Internet protocol based network.

11. The system of claim 1, wherein a least a portion of the network is the Internet.

12. The system of claim 1, wherein the digital repository comprises:
a central digital repository, and
a practitioner local digital repository remote from the central database.

13. The system of claim 12, wherein:
at least one of the practitioner local digital repository and the central digital repository is further populated with patient historical entries, the patient historical entries each associated with an individual patient and having a patient identification indicator, and at least one patient history indicator.

14. The system of claim 13, wherein the at least one patient history indicator comprises information corresponding to a medical device of the individual patient.

15. The system of claim 14, wherein the information corresponding to a medical device of an individual patient comprises an identification numberr of a component of the medical device.

16. The system of claim 13, wherein:
the patient historical entries further have at least one patient care indicator.

17. The system of claim 16, wherein the patient care indicator comprises reimbursement information.

18. The system of claim 17, wherein the reimbursement information comprises an L code indicator.

19. The system of claim 13 wherein the digital repository is configured to interface with an external system.

20. The system of claim 19, wherein the external system comprises at least one of a patient management system, a billing system, and an insurance reimbursement system.

21. The system of claim 1, wherein:
the computer readable medium is further encoded with processor readable instructions that when executed by the processor further implement a patient letter of necessity generation mechanism configured to generate a letter of necessity the patient based on information stored in the digital repository and to store the letter of necessity in the digital repository, and
the practitioner user interface mechanism is further configured to provide access to the patient letter of necessity generation mechanism.

22. The system of claim 1, wherein the digital repository comprises a database.

23. The system of claim 1, wherein the practitioner user interface is further configured to accept the at least one patient interview answer indicator from an external device.

24. The system of claim 23, wherein the external device is at least one of a digitizer, digital camera, and a digital video camera.

25. The system of claim 1 wherein:
the entries in the digital repository further have a ranking indicator, and
the configurator mechanism is further configured to select a plurality of subsets of entries from the digital repository based on the at least one patient interview answer indicator in the memory, each of the plurality of subsets including entries corresponding to individual medical device components of a medical device meeting the need of the patient and being ranked based on the ranking indicator of the entries.

26. The system of claim 25, wherein the ranking indicator comprises at least one of a component cost indicator, a component weight indicator, a component height indicator, a component width indicator, a component activity level indicator, and an inventory indicator.

27. The system of claim 25, wherein:
the computer readable medium is further encoded with processor readable instructions that when executed by the processor further implement a customization mechanism configured to select one of the plurality of subsets of entries and at least one of add, remove, and modify at least one entry of the one of the plurality of subsets of entries selected by the configurator mechanism, and
the practitioner user interface mechanism is further configured to provide access to the customization mechanism.

28. The system of claim 27, wherein:
the computer readable medium is further encoded with processor readable instructions that when executed by the processor further implement a medical device shopping mechanism configured to place an order for the medical device corresponding to the one of the plurality of subsets of entries selected by the customization mechanism and to store order information in the digital repository, and
the practitioner user interface mechanism is further configured to provide access to the medical device shopping mechanism.

29. The system of claim 27, wherein the practitioner user interface mechanism is further configured to provide a summary page of components customized by the customization mechanism.

30. The system of claim 1, wherein:
the computer readable medium is further encoded with processor readable instructions that when executed by the processor further implement a catalog mechanism configured to select a subset of entries from the digital repository based on a query and to provide the subset of entries to the practitioner user interface mechanism, and
a medical device component shopping mechanism is configured to place an order for a medical device component corresponding to at least one selected entry of the subset of entries and to store order information in the digital repository,
the practitioner user interface mechanism further configured to accept the query from a user, to provide the query to the catalog mechanism, and to select the at least one selected entry of the subset of entries provided by the catalog mechanism.

31. The system of claim 30, wherein:
the computer readable medium is further encoded with processor readable instructions that when executed by the processor further implement a customization mechanism configured to select at least one of the subsets of entries and at least one of add, remove, and modify at least one entry of the one of the plurality of subsets of entries selected by the catalog mechanism, and
the practitioner user interface mechanism is further configured to provide access to the customization mechanism.

32. The system of claim 31, wherein the practitioner user interface mechanism is further configured to provide a summary page of components customized by the customization mechanism.

33. A method for configuring a medical device, comprising the steps of:
populating a digital repository with information corresponding to a plurality of medical device components;
interviewing a patient having a need for a medical device to determine at east one patient attribute;
storing the at least one patient attribute in a memory; and
querying the digital repository for a subset of medical device components based on the at least one patient attribute, the subset of medical device components collectively forming a medical device meeting the need of the patient.

34. The method of claim 33, wherein the medical device comprises at least one of a lower extremity prosthetic device, an upper extremity prosthetic device a lower extremity orthotic device, an upper extremity orthotic device, and a spinal orthotic device.

35. The method of claim 33, further comprising the step of:
customizing at least one of the subset of medical device components to create a customized medical device further meeting the need of the patient.

36. The method of claim 33, wherein the querying step comprises:
querying the digital repository for a plurality of subsets of medical device components based on the at least one patient attribute, the subset of medical device components corresponding to a medical device meeting the need of the patient; and
ranking the plural of subsets based on a ranking criteria.

37. The method of claim 36, wherein the ranking criteria is at least one of a weight of the medical device, a height of the medical device, a width of the medical device, a cost of the medical device, an activity level supported by the medical device, and an inventory status of the medical device.

38. The method of claim 36, further comprising the step of:
selecting one of the plurality of subsets;
customizing the one of the plurality of subsets to create a customized medical device further meeting the need of the patient and ordering the customized medical device.

39. The method of claim 38, wherein the ordering step comprises reviewing the customized medical device prior to ordering.

40. The method of claim 38, wherein the ordering step comprises determining all applicable price discounts for the medical device for the practitioner.

41. The method of claim 33, wherein the interviewing step comprises entering the at least one patent attribute via at least one of a personal data assistant, a digitizer a digital camera, and a digital video camera.

42. The method of claim 33, further comprising the steps of:
customizing at least one of the subset of medical device components to create a customized medical device further meeting the need of the patient;
storing a customization result of the customizing step in the digital repository;
comparing the customization result to the subset of medical device components to identify a customization trend; and
adjusting an algorithm used in the querying step based on the customization trend causing a different subset of medical device components to be queried based on the at least one patient attribute.

43. A system for configuring a medical device, comprising:
means for populating a digital repository with information corresponding to a plurality of individual medical device components;
means for interviewing a patient having a need for a medical device to determine at least one patient attribute;
mean for storing the at least one patient attribute in a memory; and
means for querying the digital repository for a subset of medical device components based on the at least one patient attribute, the subset of medical device components collectively forming a medical device meeting the need of the patient.

44. The system of claim 43, wherein the medical device comprises at least one of a lower extremity prosthetic device, an upper extremity prosthetic device, a lower extremity orthotic device, an upper extremity orthotic device, and a spinal orthotic device.

45. The system of claim 43, further comprising:
means for customizing at least one of the subset of medical device components to create a customized medical device further meeting the need of the patient.

46. The system of claim 43, further comprising:
means for determining applicable discounts for the medical device for the practitioner.

47. A method for configuring a medical device, comprising the steps of;
populating a digital repository with information corresponding to a plurality of individual medical device components;
populating the digital repository with patent historical information associated with a patient;
interviewing the patient having a need for a medical device to determine at least one patient attribute;
storing the at least one patient attribute in a memory via a digital communication link;
querying the digital repository for a subset of medical device components based on the at least one patient attribute, the subset of medical device components, collectively forming a medical device meeting the need of the patient;

ordering the medical device over the digital communication link; and storing information corresponding to the medical device in the digital repository associated with the patient.

48. The method of claim 47, wherein the medical device comprises at least one of a lower extremity prosthetic device an upper extremity prosthetic device, a lower extremity orthotic device, an upper extremity orthotic device, and a spinal orthotic device.

49. The method of claim 47, wherein the patient historical information comprises at least one of reimbursement information and L code information.

50. The method of claim 47, further comprising the step of;

sharing information in the digital repository with an external system.

51. The method of claim 50, wherein the external system comprises at least one of a patient management system a billing system, and an insurance reimbursement system.

* * * * *

UNITED STATES PATENT AND TRADEMARK OFFICE
CERTIFICATE OF CORRECTION

| | | |
|---|---|---|
| PATENT NO. | : 7,870,005 B2 | Page 1 of 1 |
| APPLICATION NO. | : 09/893535 | |
| DATED | : January 11, 2011 | |
| INVENTOR(S) | : Robert E. Arbogast et al. | |

It is certified that error appears in the above-identified patent and that said Letters Patent is hereby corrected as shown below:

In Column 3, line 5, please delete "oftentimes" and insert -- often times --

In Column 3, line 60, please delete "medical" and insert -- medical device --

In Column 20, line 44, please delete "configurator" and insert -- a configurator --

In Column 21, line 37, please delete "a least" and insert -- at least --

In Column 22, line 9, please delete "necessity" and insert -- necessity for --

In Column 23, line 38, please delete "east" and insert -- least --

In Column 24, line 13, please delete "patent" and insert -- patient --

In Column 24, line 36, please delete "mean" and insert -- means --

In Column 24, line 60, please delete "patent" and insert -- patient --

In Column 26, line 8, please delete "system" and insert -- system, --

Signed and Sealed this
Fifth Day of April, 2011

David J. Kappos
*Director of the United States Patent and Trademark Office*